United States Patent [19]
Jones et al.

[11] Patent Number: 5,858,748
[45] Date of Patent: *Jan. 12, 1999

[54] GRAM-POSITIVE ALKALIPHILIC MICROORGANISMS

[75] Inventors: Brian Edward Jones, Va Leidschendam, Netherlands; William Duncan Grant, Leicester; Nadine Claire Collins, Dorking, both of United Kingdom

[73] Assignee: Genencor International, Inc., Rochester, N.Y.

[ * ] Notice: The term of this patent shall not extend beyond the expiration date of Pat. No. 5,514,575.

[21] Appl. No.: 914,736

[22] Filed: Aug. 19, 1997

Related U.S. Application Data

[60] Division of Ser. No. 314,045, Sep. 28, 1994, Pat. No. 5,707,851, which is a continuation-in-part of Ser. No. 903,786, Jun. 24, 1992, Pat. No. 5,401,657.

[51] Int. Cl.$^6$ .............................. C12N 1/20; C12N 9/28; C12N 9/52; C12N 9/00
[52] U.S. Cl. ........................ 435/183; 435/190; 435/195; 435/196; 435/197; 435/198; 435/200; 435/202; 435/210; 435/220; 435/221; 435/252.1; 435/252.31; 435/252.4
[58] Field of Search ..................... 435/183, 195, 435/220, 221, 190, 196, 197, 198, 202, 227, 252.1, 201, 210, 252.31, 252.4

[56] References Cited

U.S. PATENT DOCUMENTS

| | | | |
|---|---|---|---|
| 5,401,657 | 3/1995 | Jones et al. | 435/252.1 |
| 5,514,575 | 5/1996 | Jones et al. | 435/198 |

*Primary Examiner*—Herbert J. Lilling
*Attorney, Agent, or Firm*—Morrison & Foerster LLP

[57] ABSTRACT

The present invention provides novel aerobic, Gram-positive alkaliphilic bacteria which have been isolated from in and around alkaline soda lakes. These alkaliphiles have been analyzed according to the principles of numerical taxonomy with respect to each other and also to a collection of known bacteria. In addition, these bacterial taxa are further circumscribed by an analysis of the lipid components which serve as chemotaxonomic markers. The alkaliphiles of the present invention produce alkalitolerant enzymes which are capable of performing their functions at high pH which makes them uniquely suited for applications requiring such extreme conditions.

21 Claims, 4 Drawing Sheets

GRAM-POSITIVE ALKALIPHILIC MICROORGANISMS

This application is a divisional of prior application Ser. No. 08/314,045, filed Sep. 28, 1994, now U.S. Pat. No. 5,707,851; which is a continuation-in-part of prior application Ser. No. 07/903,786, filed Jun. 24,1992, now U.S. Pat. No. 5,401,657.

The present invention is in the field of microbiology and more particularly in the field of alkaliphilic microorganisms.

BACKGROUND OF THE INVENTION

Alkaliphiles are defined as organisms which exhibit optimum growth in an alkaline pH environment, particularly in excess of pH 8, and generally in the range between pH 9 and 10. Alkaliphiles may also be found living in environments having a pH as high as 12. Obligate alkaliphiles are incapable of growth at neutral pH.

Alkaliphiles may be found in certain everyday environments such as garden soil, presumably due to transient alkaline conditions caused by biological activities including ammonification, sulphate reduction or photosynthesis. A much richer source of a greater variety of alkaliphilic organisms may be found in naturally occurring, stable alkaline environments such as soda lakes.

A more detailed study of soda lakes and alkaliphilic organisms in general is provided in Grant, W. D., Mwatha, W. E. and Jones, B. E. ((1990) FEMS Microbiology Reviews, 75, 255–270), the text of which is hereby incorporated by reference. Lists of alkaline soda lakes may be found in the publications of Grant, W. D. and Tindall, B. J. in *Microbes in Extreme Environments*, (eds. R. A. Herbert and G. A. Codd); Academic Press, London, (1986), pp. 22–54); and Tindall, B. J. in *Halophilic Bacteria*, Volume 1, (ed. F. Rodriguez-Valera); CRC Press Inc., Boca Raton, Fla., (1988), pp. 31–70, both texts are also hereby incorporated by reference.

Alkaliphiles, the majority of which are Bacillus species, have been isolated from non-saline environments and are discussed by Horikoshi, K. and Akiba, T. in *Alkalophilic Microorganisms* (Springer-Verlag, Berlin, Heidelberg, N.Y., (1982)). However, alkaliphilic organisms from saline and alkaline environments such as lakes are not discussed therein. Strictly anaerobic bacteria from alkaline, hypersaline, environments have been recently described by Shiba, H. in *Superbugs* (eds. K. Horikoshi and W. D. Grant); Japan Scientific Societies Press, Tokyo and Springer-Verlag, Berlin, Heidelberg, N.Y., (1991) pp. 191–211; and by Nakatsugawa. N., ibid, pp. 212–220.

Soda lakes, which may be found in various locations around the world, are caused by a combination of geological, geographical and climatic conditions. They are characterized by the presence of large amounts of sodium carbonate (or complexes thereof) formed by evaporative concentration, as well as by the corresponding lack of $Ca^{2+}$ and $Mg^{2+}$ which would remove carbonate ions as insoluble salts. Other salts such as NaCl may also concentrate resulting in environments which are both alkaline and saline.

Despite this apparently harsh environment, soda lakes are nevertheless home to a large population of prokaryotes, a few types of which may dominate as permanent or seasonal blooms. The organisms range from alkaliphilic cyanobacteria to haloalkaliphilic archaeabacteria. Moreover, it is not unusual to find common types of alkaliphilic organisms inhabiting soda lakes in various widely dispersed locations throughout the world such as in the East African Rift Valley, in the western U.S., Tibet, China and Hungary. For example, natronobacteria have been isolated and identified in soda lakes located in China (Wang, D. and Tang, Q., "Natronobacterium from Soda Lakes of China" in *Recent Advances in Microbial Ecology* (Proceedings of the 5th International Symposium on Microbial Ecology, eds. T. Hattori et al.); Japan Scientific Societies Press, Tokyo, ((1989), pp. 68–72) and in the western U.S. (Morth, S. and Tindall, B. J. (1985) System. Appl. Microbiol., 6, pp. 247–250). Natronobacteria have also been found in soda lakes located in Tibet (W. D. Grant, unpublished observations) and India (Upasani, V. and Desai, S. (1990) Arch. Microbiol., 154, pp. 589–593)

Alkaliphiles have already made an impact in the application of biotechnology for the manufacture of consumer products. Alkalitolerant enzymes produced by alkaliphilic microorganisms have already found use in industrial processes and have considerable economic potential. For example, these enzymes are currently used in detergent compositions and in leather tanning, and are foreseen to find applications in the food, waste treatment and textile industries. Additionally, alkaliphiles and their enzymes are potentially useful for biotransformations, especially in the synthesis of pure enantiomers. Also, many of the microorganisms described herein are brightly pigmented and are potentially useful for the production of natural colorants.

SUMMARY OF THE INVENTION

The present invention concerns novel aerobic, Gram-positive alkaliphilic bacteria. These bacteria have been isolated from samples of soil, water, sediment and a number of other sources, all of which were obtained from in and around alkaline soda lakes. These alkaliphiles have been analyzed according to the principles of numerical taxonomy with respect to each other and also to a collection of known bacteria in order to confirm their novelty. In addition, these bacterial taxa are further circumscribed by an analysis of the lipid components which serve as chemotaxonomic markers.

The present invention also provides data as to the composition of the environments from which the samples containing the microorganisms were obtained, as well as the media required for their efficient isolation and culture such that one of ordinary skill may easily locate such an environment and be able to isolate the organisms of the present invention by following the procedures described herein.

It is also an object of the present invention to provide microorganisms which produce alkalitolerant enzymes. These enzymes are capable of performing their functions at high pH which makes them uniquely suited for applications requiring such extreme conditions. For example, alkalitolerant enzymes may be employed in detergent compositions, in leather tanning and in the food, waste treatment and textile industries, as well as for biotransformations such as the production of pure enantiomers and the production of natural pigments.

The genes encoding these alkalitolerant enzymes may be isolated, cloned and brought to expression in compatible expression hosts to provide a source of larger yields of enzyme products which may be, if desired, more easily purified and used in various industrial applications, should the wild-type strain fail to produce sufficient amounts of the desired enzyme, or performs poorly under normal industrial fermentation conditions.

DETAILED DESCRIPTION OF THE INVENTION

Sampling

Several hundreds of strains of bacteria have been isolated from samples of soil, water, sediment and a number of other sources in and around alkaline lakes. These samples were obtained as part of an investigation over a period of three years. The isolated bacteria are non-phototrophic eubacteria. Until now, such bacteria have not been well characterized.

The samples were collected in sterile plastic bags. Sampling was conducted at lakes Elmenteita, Nakuru, Bogoria, Crater (Sonachi), Little Naivasha (Oloidien) and Magadi, all of which are located in Kenya, East Africa. Alkaline soda lakes having similar environments may also be found in Tibet, China, Hungary and the western U.S. At each sampling site, the physical appearance of the site and the sample were described and physical parameters such as pH, conductivity and temperature were measured. Some of the samples were treated locally within 36 hours of collection of the samples but the majority were examined off-site, several weeks after collection.

Table 1 lists various strains which have been isolated. The strains are listed according to the location from which the sample was taken and the physical appearance of the sample itself.

Table 2 provides examples of typical chemical analyses of the lake waters at the sampling locations at the time of extraction of many of the samples. These data are consistent with earlier analyses (Grant, W. D. and Tindall, B. J., supra).

Figure 1:
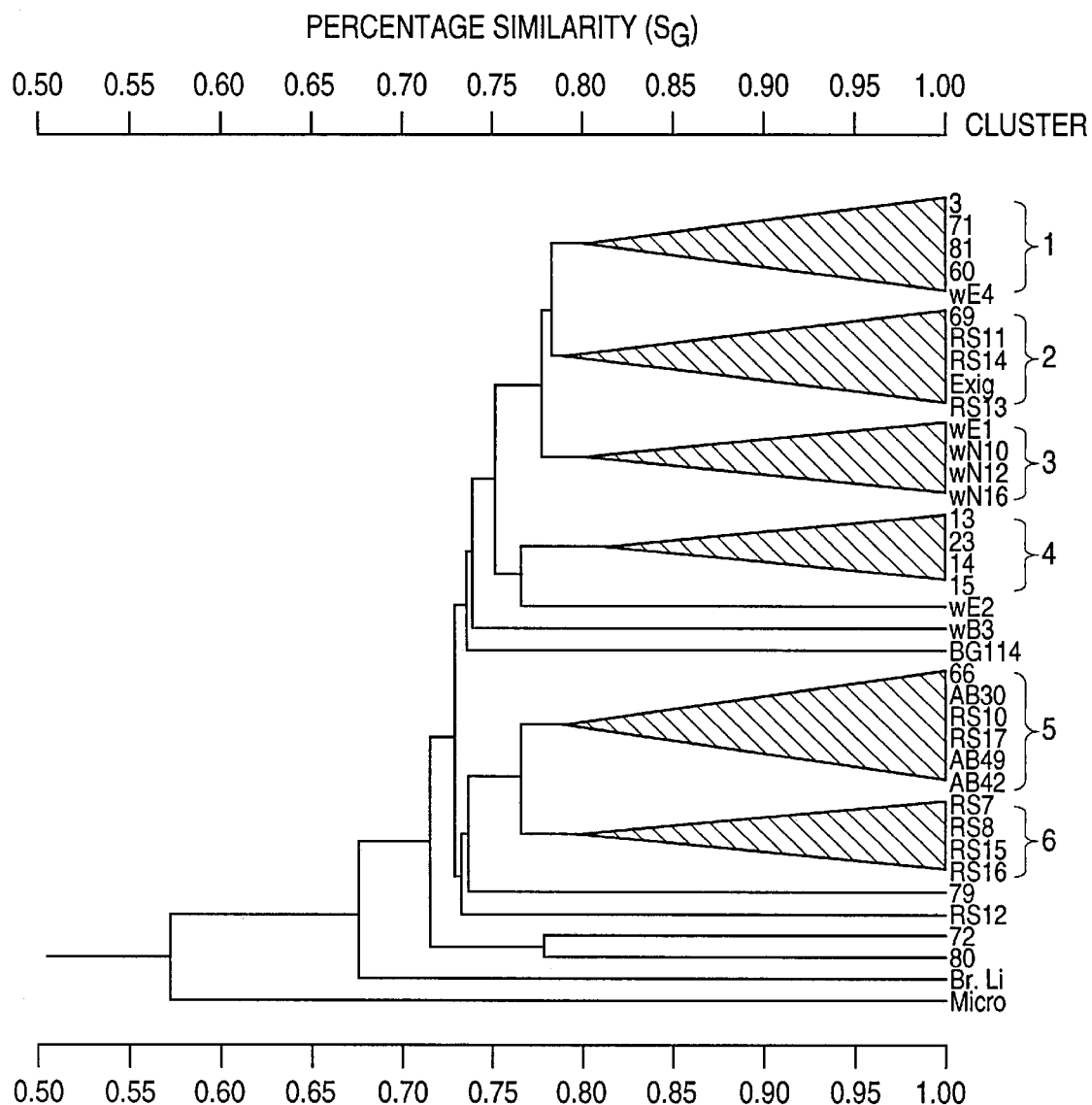
FIG. 1. Simplified dendrogram showing clusters (phenons) obtained with the $S_G$ coefficient and Unweighted Average Linkage procedure.

Table 3 provides a list of the isolated strains arranged according to the results of the numerical taxonomic analysis (FIG. 1). Furthermore, Table 3 provides physical properties of the original sample, in particular the temperature, conductivity and alkaline pH, as well as the numerous isolation media required for obtaining pure cultures of these novel bacteria. These media are letter coded with reference to Appendix A.

Tables 1, 2 and 3 provide data from which the environment of the sampling locations may be characterized. The chemical and physical analyses of the samples confirm the presence of alkaline pH, as well as the presence of unusually high levels of $Na_2CO_3$, coupled with low levels of $Ca^{2+}$ and $Mg^{2+}$. It is known that the basic environments of soda lakes are stable with respect to their pH and ionic composition. Moreover, the microbial populations found at these sites remain largely stable. Thus, it is to be expected that the environment from which bacteria according to the present invention may be obtained can be determined from the data presented in Tables 1–3.

The fresh soda-lake water samples were plated out on an alkaline nutrient medium (Medium A) soon after collection. Microscopic inspection of the soda lake samples showed a surprisingly high diversity of bacterial types. considering the extremely alkaline nature of the environment, viable counts showed unexpectedly high numbers of organotrophic bacteria, in the range of $10^5$–$10^6$ colony forming units per ml. The samples were stored either cooled or at ambient temperatures. After a few weeks' storage, the total numbers of bacteria in the sample rose, whereas the diversity of types decreased.

TABLE 1

Alkaliphilic Strains Arranged According to Their Place of Origin

| STRAINS | SAMPLE LOCATION | SAMPLE APPEARANCE |
| --- | --- | --- |
| 3E.1 | Lake Elmenteita (east bay). | Mud from dried up lake bed. |
| wE1, wE2, wE4 | Lake Elmenteita (east bay). | Sediment and water, littoral zone. |
| 60E.4 | Lake Elmenteita (east bay). | Mud, littoral zone. |
| wN10, wN12, wN16 | Lake Nakuru, north beach between Hippo Point and Njoro Point. | Mud and water, littoral zone. |
| wB3 | Lake Bogoria, northern mud flats. | Mud and water, littoral zone. |
| 66B.4 | Lake Bogoria (west shore), Loboru delta area. | Soda crusts and mud (around hot spring). |
| 69B.4 | Lake Bogoria (south bay). | Water column and sediment, littoral zone. |
| 13C.1, 71C.4, 72C.4 | Crater Lake (north point). | Mud and water, littoral zone. |
| 14LN.1, 15LN.1, 79LN.4 | Little Lake Naivasha (south shore). | Water column and sediment |
| 80LN.4, 81LN.4 | Little lake Naivasha (south shore). | Black mud, benthic zone. |
| 23M.1 | Lake Magadi (causeway, upper western arm). | Mud and water. |

TABLE 2

Typical Chemical Analysis of Kenyan Lake Waters[+]

| Lake | $Na^+$ (mM) | $K^+$ (mM) | $Ca^{2+}$ (mM) | $Mg^{2+}$ (mM) | $SiO_2$ (mM) | $PO_4^{3-}$ (mM) | $Cl^-$ (mM) | $SO_4^{2-}$ (mM) | $CO_3^{2-}$ (mM) | TON* (mM) | TA§ |
| --- | --- | --- | --- | --- | --- | --- | --- | --- | --- | --- | --- |
| Elmenteita | 196 | 3.58 | 0.07 | b.l.d. | 2.91 | 0.03 | 65.1 | 2.0 | 68.0 | 0.8 | 119 |
| Nakuru | 326 | 5.63 | 0.15 | b.l.d. | 3.25 | 0.15 | 57.5 | 0.5 | 198.3 | 1.9 | 259 |
| Bogoria | 796 | 6.78 | 0.19 | 0.01 | 1.98 | 0.17 | 115.5 | 1.1 | 516.7 | 0.5 | 669 |

TABLE 2-continued

Typical Chemical Analysis of Kenyan Lake Waters[+]

| Lake | $Na^+$ (mM) | $K^+$ (mM) | $Ca^{2+}$ (mM) | $Mg^{2+}$ (mM) | $SiO_2$ (mM) | $PO_4^{3-}$ (mM) | $Cl^-$ (mM) | $SO_4^{2-}$ (mM) | $CO_3^{2-}$ (mM) | TON* (mM) | TA§ |
|---|---|---|---|---|---|---|---|---|---|---|---|
| Crater | 140 | 8.95 | 0.06 | 0.01 | 2.13 | 0.04 | 12.4 | 0.8 | 90.0 | 1.1 | 133 |
| Little Naivasha | 8.7 | 1.79 | 0.28 | 0.65 | 1.02 | 0.003 | 4.8 | 0.5 | <10.0 | <0.07 | 18 |
| Magadi | 2826 | 26.1 | 0.03 | 0.01 | 7.1 | 0.23 | 1124 | 12.8 | 1816 | 5.4 | 180 | b.l.d. = below the limits of detection
*= Total Organic Nitrogen
§= Total Alkalinity in milliequivalents/liter
[+]= October 1988

TABLE 3

Origin of the Strains Arranged by Cluster

| | | SAMPLE | | | | |
|---|---|---|---|---|---|---|
| CLUSTER | STRAIN | LOCATION | pH | Temp. 0° | Conductivity mS/cm | ISOLATION MEDIUM |
| 1 | 3E.1[CT] | Elmenteita | 9.5 | 35 | 2 | A |
| 1 | 71C.4 | Crater | 10 | 26 | 10.2 | E |
| 1 | 81LN.4 | Little Naivasha | 8.5–9 | 30 | 1.2 | D |
| 1 | 60E.4 | Elmenteita | 10 | 32 | 12.7 | B |
| 1 | wE4 | Elmenteita | n.t. | n.t. | n.t. | A |
| 2 | 69B.4 | Bogoria | 10.5 | 33 | 44 | C |
| 2 | RS11[CT] | | | | | * |
| 2 | RS14 | | | | | * |
| 2 | Exig. | | | | | * |
| 2 | RS13 | | | | | * |
| 3 | wE1 | Elmenteita | n.t. | n.t. | n.t. | A |
| 3 | wN10 | Nakuru | n.t. | n.t. | n.t. | A |
| 3 | wN12 | Nakuru | n.t. | n.t. | n.t. | A |
| 3 | wN16[CT] | Nakuru | n.t. | n.t. | n.t. | A |
| 4 | 13C.1 | Crater | 9.0 | 30 | 10 | A |
| 4 | 23M.1 | Magadi | 11 | 36 | 100 | A |
| 4 | 14LN.1 | Little Naivasha | 8.5 | 26 | 1 | A |
| 4 | 15LN.1[CT] | Little Naivasha | 8.5 | 26 | 1 | A |
| — | wE2 | Elmenteita | n.t. | n.t. | n.t. | A |
| — | wB3 | Bogoria | n.t. | n.t. | n.t. | A |
| — | BG114 | | | | | * |
| 5 | 66B.4 | Bogoria | n.t. | n.t. | n.t. | F |
| 5 | AB30 | | | | | * |
| 5 | RS10[CT] | | | | | * |
| 5 | RS17 | | | | | * |
| 5 | AB49 | | | | | * |
| 5 | AB42 | | | | | * |
| 6 | RS7 | | | | | * |
| 6 | RS8[CT] | | | | | * |
| 6 | RS15 | | | | | * |
| 6 | RS16 | | | | | * |
| — | 79LN.4 | Little Naivasha | 8.5–9 | 30 | 1.2 | F |
| — | RS12 | | | | | * |
| — | 72C.4 | Crater | 10 | 26 | 10.2 | E |
| — | 80LN.4 | Little Naivasha | 8.5–9 | 30 | 1.2 | G |
| — | Br.li | | | | | * |
| — | Micro | | | | | * | n.t. = not tested
The letter codes given for the Isolation Media refer to Appendix A.
The asterisk (*) refers to a reference strain; the identity of which is provided in Table 4 (below).

Treatment of the Samples: Enrichment and Isolation of Alkaliphilic Bacteria

A wide diversity of enrichment and isolation methods were applied. Some of the methods were specifically designed for the enrichment and isolation of alkaliphilic bacteria which exhibit specific types of enzyme activity at an alkaline pH. Other techniques of a more general nature were applied for the isolation of diverse sorts of alkaliphilic bacteria. In some cases, the specific conditions prevailing in the lakes (Table 2) were taken into account when experiments were performed for the isolation of bacteria.

The different nutrient media employed for the isolation of the new alkaliphilic bacteria are designated Medium A–Medium G. The composition of the various media employed is shown in Appendix A.

For the isolation of non-specific alkaliphilic organotrophic bacteria, soda-lake water samples or dilutions thereof were streaked out on an alkaline nutrient agar, pH 10–pH 10.5 (Medium A). Samples of a more solid consistency, mud, sediment, etc. were first suspended in an alkaline nutrient broth (Medium A) before spreading on an alkaline nutrient agar (Medium A). The bacteria were cultivated in a heated incubator, preferably at 37° C. In some cases, the samples were suspended in an alkaline nutrient broth (Medium A) and the bacteria cultivated by shaking, preferably at 37° C. for 2–3 days before spreading the broth onto an alkaline nutrient agar (Medium A) for the isolation of bacterial colonies.

For the isolation of alkaliphilic bacteria exhibiting specific types of enzyme activity, samples were spread onto alkaline nutrient agar containing specific substrates such as lactalbumin or casein or olive oil. In some instances, the bacteria in the sample were enriched for 1 day up to several weeks in a non-specific alkaline nutrient broth such as Medium A before spreading the broth onto an alkaline nutrient agar specific for the detection of bacteria exhibiting enzyme activities such as lipolytic or proteolytic activity.

Taxonomic Analysis

Twenty strains of bacteria isolated from in and around alkaline lakes were assigned to the type of bacteria known as Gram-positive bacteria on the basis of (1) the Dussault modification of the Gram's staining reaction (Dussault, H. P., (1955), Journal of Bacteriology, 70, 484–485); (2) the KOH sensitivity test (Gregersen, T., (1978), European Journal of Applied Microbiology and Biotechnology 5, 123–127; Halebian, S. et al., (1981), Journal of Clinical Microbiology, 13, 444–448); (3) the aminopeptidase reaction (Cerny, G., (1976), European Journal of Applied Microbiology, 3, 223–225; ibid, (1978), 5, 113–122); and in most cases, confirmation also on the basis of (4) a quinone analysis (Collins, M. D. and Jones, D., (1981), Microbiological Reviews, 45, 316–354) using the method described by Collins, M. D. in *Chemical Methods in Bacterial Systematics* (eds. Goodfellow, M. and Minnikin, D.) pp. 267–288, Academic Press, London, 1985.

The twenty strains were tested for 200 characters. The results were analyzed using the principles of numerical taxonomy (Sneath, P. H. A. and Sokal, R. R., in *Numerical Taxonomy*, W. H. Freeman & Co., San Francisco, 1973). The characters tested and manner of testing are compiled in Appendix B. In addition, Appendix C records how each character was coded for taxonomic analysis.

As controls, 17 known Gram-positive bacteria were subjected to the same analysis using the same conditions where appropriate. These reference bacteria included genera that are known to include facultative or obligate alkaliphilic species. These 17 known reference bacteria are recorded in Table 4 from which it will be seen that the "Type Strain" of the known species has been used where available. Thirteen of the strains are known alkaliphilic Bacillus species.

TABLE 4

Gram-Positive Reference Strains

| * | |
|---|---|
| (RS7) | (alkaliphilic) Bacillus species DSM 2514 |
| (RS8) | (alkaliphilic) Bacillus species DSM 2515 |
| (RS10) | (alkaliphilic) Bacillus species DSM 2517 |
| (RS11) | (alkaliphilic) Bacillus species DSM 2518 |
| (RS12) | (alkaliphilic) Bacillus species DSM 2519 |
| (RS13) | (alkaliphilic) Bacillus species DSM 2521 |
| (RS14) | (alkaliphilic) Bacillus species DSM 2523 |
| (RS15) | (alkaliphilic) Bacillus species DSM 2525 |
| (RS16) | *Bacillus alcalophilus*$^T$ DSM 485 |
| (RS17) | *Bacillus alcalophilus subsp. halodurans* DSM 497 |
| (AB30) | (alkaliphilic) Bacillus species ATCC 21596 |
| (AB42) | (alkaliphilic) Bacillus species ATCC 21833 |
| (AB49) | (alkaliphilic) Bacillus species ATCC 21591 |
| (Exig) | *Exiguobacterium aurantiacum*$^T$ NCIMB 11798 |
| (BG114) | *Arthrobacter luteus* ATCC 21596 |
| (Br.li) | *Brevibacterium linens*$^T$ NCIMB 9904 |
| (Micro) | *Micrococcus luteus*$^T$ NCTC 2665 |

Figure 2:
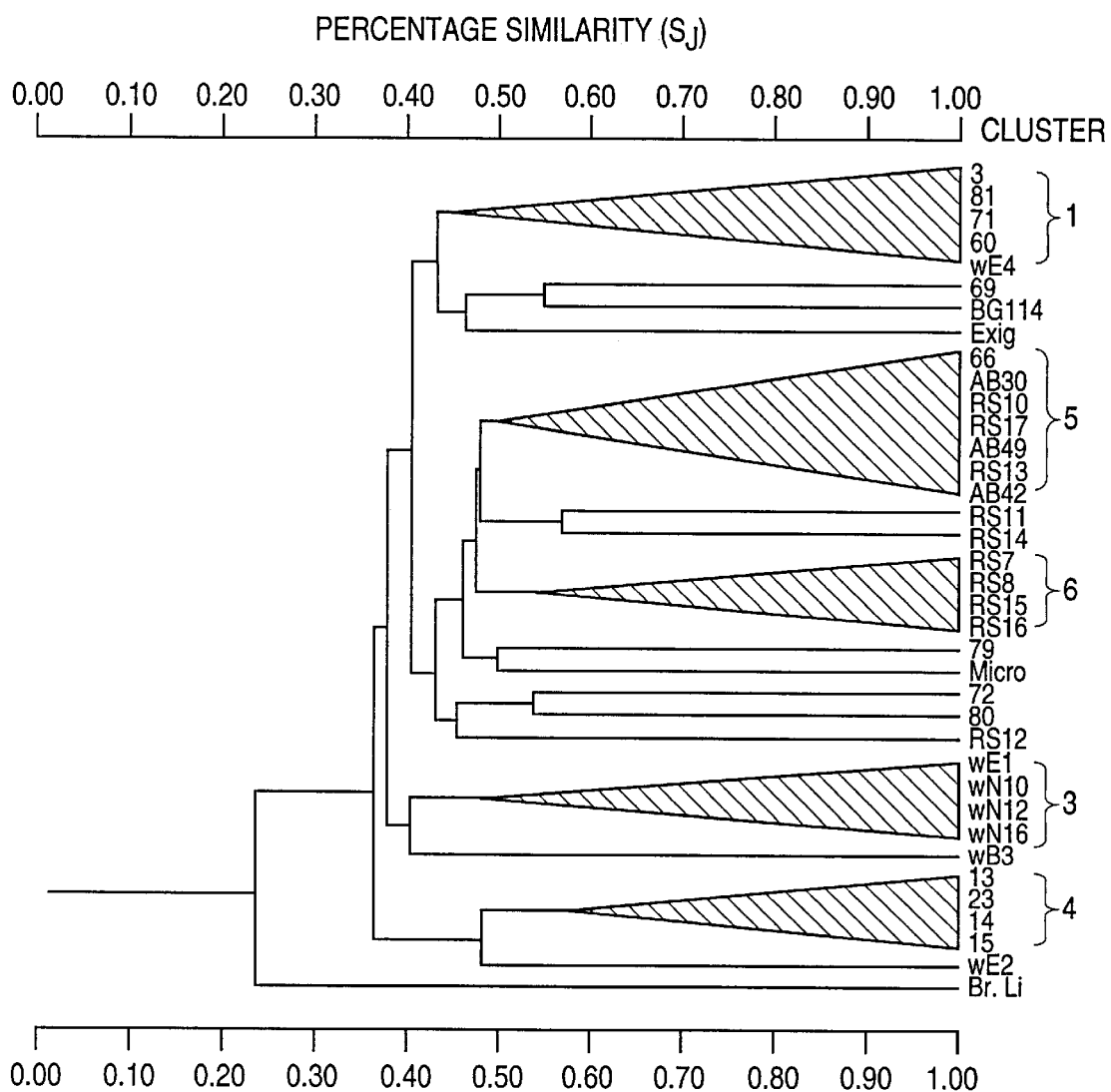
FIG. 2. Simplified dendrogram showing clusters (phenons) obtained with the $S_J$ coefficient and Unweighted Average Linkage procedure.
Figure 3:
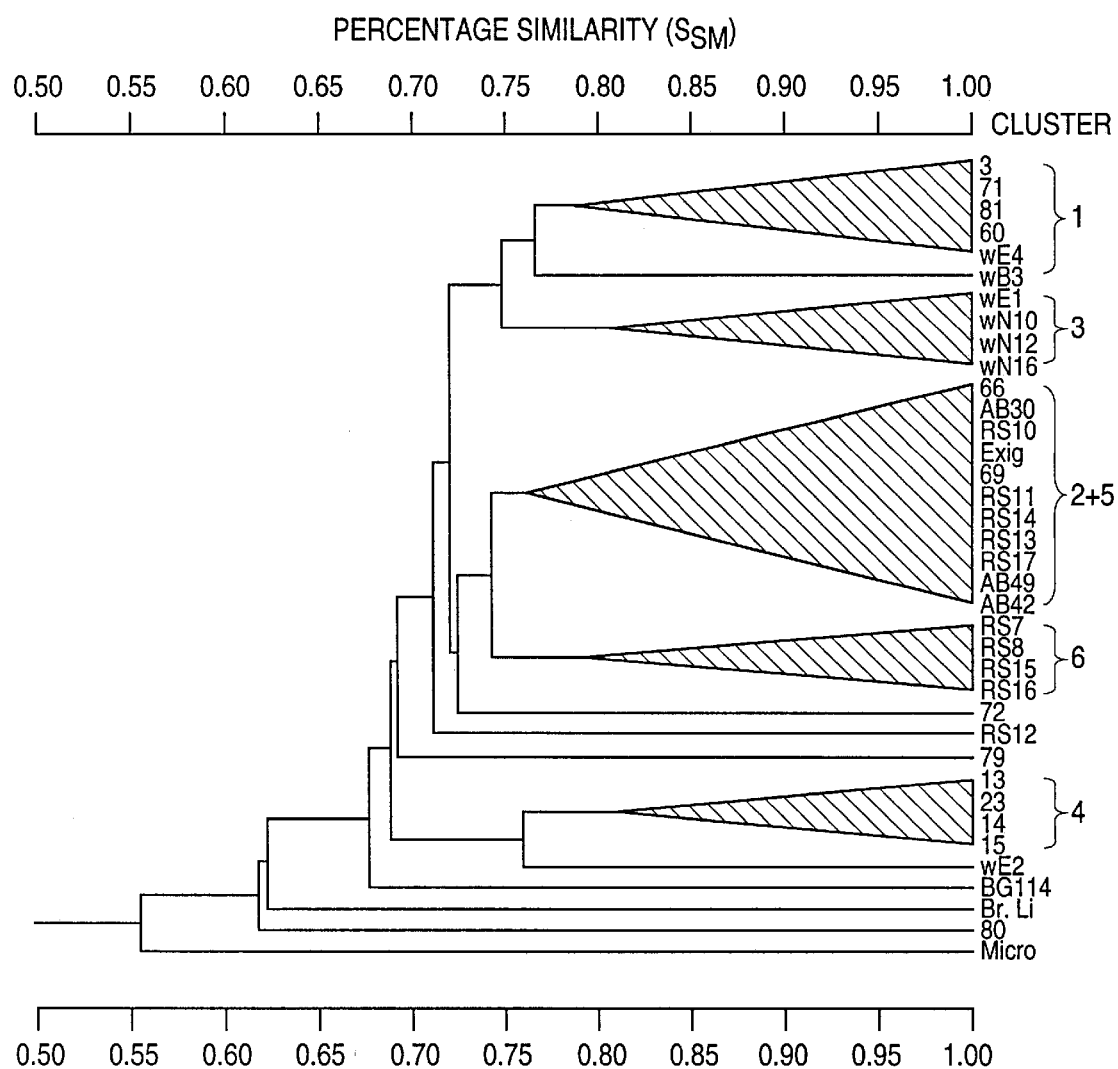
FIG. 3. Simplified dendrogram showing clusters (phenons) obtained with the $S_{SM}$ coefficient and Unweighted Average Linkage procedure.

*abbreviation used in FIG. 1, FIG. 2 and FIG. 3
$^T$denotes "Type Strain"

Analysis of Test Data
The Estimation of Taxonomic Resemblance

The phenetic data, consisting of 200 unit characters was scored as indicated in Appendix C, and set out in the form of an "nxt" matrix, whose t columns represent the t bacterial strains to be grouped on the basis of resemblances, and whose n rows are the unit characters. Taxonomic resemblance of the bacterial strains was estimated by means of a similarly coefficient (Sneath, P. H. A. and Sokal, R. R., *Numerical Taxonomy*, supra, pp. 114–187). Although many different coefficients have been used for biological classification, only a few have found regular use in bacteriology. We have chosen to apply three association coefficients (Sneath, P. H. A. and Sokal, R. R., ibid, p. 129 et seq.), namely, the Gower, Jaccard and Simple Matching coefficients. These have been frequently applied to the analysis of bacteriological data and have a wide acceptance by those skilled in the art since they have been shown to result in robust classifications.

The coded data were analyzed using the TAXPAK program package (Sackin, M. J., "Programmes for classification and identification". In *Methods in Microbiology*, Volume 19 (eds. R. R. Colwell and R. Grigorova), pp. 459–494, Academic Press, London, (1987)) run on a DEC VAX computer at the University of Leicester, U.K.

A similarity matrix was constructed for all pairs of strains using the Gower Coefficient ($S_G$) with the option of permitting negative matches (Sneath, P. H. A. and Sokal, R. R., supra, pp. 135–136) using the RTBNSIM program in TAXPAK. As the primary instrument of analysis and the one upon which most of the arguments presented herein are based, the Gower Coefficient was chosen over other coefficients for generating similarity matrices because it is applicable to all types of characters or data, namely, two-state, multistate (ordered and qualitative), and quantitative.

Cluster analysis of the similarity matrix was accomplished using the Unweighted Pair Group Method with Arithmetic Averages (UPGMA) algorithm, also known as the Unweighted Average Linkage procedure, by running the SMATCLST sub-routine in TAXPAK.

The result of the cluster analysis is a dendrogram, a simplified version of which is provided in FIG. 1. The dendrogram illustrates the levels of similarity between the bacterial strains. The dendrogram is obtained by using the DENDGR program in TAXPAK.

The phenetic data, omitting multistate characters (characters 1–5, 12, 13; Appendix C) and thus consisting of 193 unit characters, and scored in binary notation (positive= 1, negative=0) were re-analyzed using the Jaccard Coefficient ($S_J$) (Sneath, P. H. A. and Sokal, R. R., ibid, p. 131) and Simple Matching Coefficient ($S_{SM}$) (Sneath, P. H. A. and Sokal, R. R., ibid, p. 132) by running the RTBNSIM program in TAXPAK. A further two dendrograms were obtained by using the SMATCLST with UPGMA option and DENDGR sub-routines in TAXPAK. Simplified versions of these dendrograms are illustrated in FIG. 2 and FIG. 3 respectively.

Results of the Cluster Analysis
$S_G$/UPGMA Method

FIG. 1 illustrates the results of the cluster analysis, based on the Gower Coefficient and the UPGMA method, of 20 Gram-positive, alkaliphilic bacteria isolated from in and around alkaline lakes, together with 17 known Gram-positive bacteria, including 14 alkaliphilic species.

Six natural clusters or phenons of alkaliphilic bacteria are generated at the 79% similarity level. These six clusters include 15 of the 20 alkaliphilic bacteria isolated from alkaline lakes. Although the choice of 79% for the level of delineation may seem arbitrary, it is in keeping with current practices in numerical taxonomy (Austin, B. and Priest, F., in *Modern Bacterial Taxonomy*, p. 37; Van Nostrand Reinhold; wokingham, U.K., (1986)). Placing the delineation at a lower percentage would combine groups of clearly unrelated organisms whose definition is not supported by the data. At the 79% level, 3 of the clusters exclusively contain novel alkaliphilic bacteria representing 13 of the newly isolated strains, and these may represent new taxa.

As expected, the cluster analysis groups the control Bacillus species in 3 distinct clusters which are separate from the novel alkaliphilic bacteria of the present invention. These results broadly concur with a taxonomic analysis of alkaliphilic Bacillus strains reported by Fritze, D., et al. (International Journal of Systematic Bacteriology, (1990), 40, 92–97)). None of the known organisms are significantly related to any of the 3 clusters of new, Gram-positive alkaliphilic bacteria. A clear discrimination between these clusters is possible using the concept of the minimum discriminatory tests (see below) and chemotaxonomic information (see below).

The significance of the clustering at this level is supported by the results of the TESTDEN program. This program tests the significance of all dichotomous pairs of clusters (comprising 4 or more strains) in a UPGMA generated dendrogram with squared Euclidean distances, or their complement as a measurement and assuming that the clusters are hyperspherical. The critical overlap was set at 0.25%. As can be seen from Table 5, the separation of the clusters is highly significant.

TABLE 5

Significance of the Clusters Generated by the $S_G$/UPGMA Method Provided by TESTDEN

| CLUSTER | separates from | CLUSTER | at Significance level |
|---|---|---|---|
| 1 | | 2 | P = 0.99 |
| 2 | | 3 | 0.99 < P > 0.95 |
| 3 | | 4 + wE2 | P = 0.99 |
| 5 | | 6 | P = 0.99 |

The cophenetic correlation is 0.804 which indicates the high degree of reliability with which this dendrogram represents the true taxonomic structure. (Sneath, P. H. A. and Sokal, R. R., supra, pp. 277–280, 304). Furthermore, the pattern of clusters obtained using the Jaccard Coefficient (FIG. 2 and below) and Simple Matching Coefficient (FIG. 3 and below) support the conclusions drawn here.

Two of the newly isolated alkaliphiles, 69B.4 and 66B.4 cluster among the alkaliphilic Bacillus species and may properly be considered to belong to the genus Bacillus. However, five of the new alkaliphilic strains fall outside the major clusters. Two of these, wE2 and wB3, associate at the periphery of the clusters representing the major groups of novel alkaliphilic bacteria. Strain 79LN.4 and the related pair 72C.4 and 80LN.4 are also non-clustering. Their interrelationships are more difficult to define but they probably represent new phenons presently not described.

$S_J$/UPGMA and $S_{SM}$/UPGMA Methods

The $S_J$ coefficient is a useful adjunct to the $S_G$ coefficient as it can be used to detect phenons in the latter that are based on negative matches or distortions owing to undue weight being put on potentially subjective qualitative data. Consequently, the $S_J$ coefficient is useful for confirming the validity of clusters defined initially by the use of the $S_G$ coefficient. The Jaccard Coefficient is particularly useful in comparing biochemically unreactive organisms (Austin, B. and Priest, F. G., supra, p. 37). There may be doubts about the admissability of matching negative character states (Sneath, P. H. A., and Sokal, R. R., supra, p. 131) in which case the Simple Matching Coefficient is a widely applied alternative.

In the main, all of the clusters (especially the clusters of the new bacteria) generated by the $S_G$/UPGMA method are recovered in the dendrograms produced by the $S_J$/UPGMA method (cophenetic correlation, 0.795)(FIG. 2) and the $S_{SM}$/UPGMA method (cophenetic correlation, 0.814) (FIG. 3). The main effect of these transformations is to gather all the Bacillus strains in a single large cluster which further serves to emphasize the separation between the alkaliphilic Bacillus species and the new alkaliphilic bacteria, and the uniqueness of the latter.

Chemotaxonomic Definition of the Clusters

Chemotaxonomy is the study of the chemical variations of cells in relation to systematics. The analysis of chromosomal DNA, ribosomal RNA, proteins, cell walls and membranes, for example, can give valuable insights into taxonomic relationships and may be used as a further tool to classify or to verify the taxonomy of microorganisms (Goodfellow, M. and Minnikin, D. E. in *Chemical Methods in Bacterial Systematics*, (eds. Goodfellow, M. and Minnikin, D. E.), Academic Press, London and Orlando, Fla., (1985), pp. 1–15). However, it is not always possible to decide a priori which type of chemical information will be most diagnostic for a given classification. The amphipathic polar lipids, the major respiratory quinones, the fatty acids located in the bacterial membranes and the DNA base composition all have taxonomic significance for the classification of various bacteria (Lechevalier, H. and Lechevalier, M. P., in *Microbial Lipids*, volume 1 (eds. Ratledge, C. and Wilkinson, S. G.) Academic Press, London and San Diego, Calif., (1988), pp. 869–902).

Polar Lipids

The extraction of polar lipids from bacteria and their analysis by two dimensional thin layer chromatography (2D-TLC) may yield patterns of diagnostic value. Stationary phase cells were extracted in 1:1 (v/v) $CHCl_3:CH_3OH$ and examined by 2D-TLC as described by Ross, H. N. M., Grant, W. D. and Harris, J. E., in *Chemical Methods in Bacterial Systematics*, (eds. Goodfellow, M. and Minnikin, D. E.), Academic Press, London and Orlando, Fla., (1985), pp. 289–300. The types of lipids present on the chromatograms were visualized using a variety of differential stains (Ross, H. N. M., et al., supra, p. 291, and Trincone, A., et al., Journal of General Microbiology, (1990), 136, pp. 2327–2331). The identity of components were confirmed by co-chromatography.

The results of this analysis for representative strains of Gram-positive alkaliphiles are set out in Table 6. These show no clear polar lipid pattern which is distinct for any one cluster, although they do confirm that phosphatidylethanolamine is a characteristic phospholipid of many Bacillus species, (O'Leary, W. M. and Wilkinson, S. G., in *Microbial Lipids*, volume 1, supra, p. 157). However, we were surprised to find that many of the bacteria contained one or several glycolipids. Glycolipids have not previously been demonstrated to be present in alkaliphilic bacteria (Krulwich, T. A., et al., CRC Critical Reviews in Microbiology, (1988), 16, 15–36). Furthermore, as judged by co-chromatography of several strains, all glycolipid-containing strains contained a glycolipid also found in Gram-negative alkaliphiles isolated from soda lakes. Some of the other glycolipids appear to be common to certain clusters of Gram-positive alkaliphiles. It is possible therefore, that the chemical structures of the glycolipids will be chemotaxonomic markers for many obligate alkaliphiles in general and for specific groups in particular.

TABLE 6

Polar Lipid Components of Gram-Positive Alkaliphilic Bacteria

| CLUSTER | STRAIN | PG | DPG | PGP | PI | PE | GL |
|---|---|---|---|---|---|---|---|
| 1 | 3E.1$^{CT}$ | + | + | + | | | 3+ |
| | 71C.4 | + | + | + | + | + | + |
| | 81LN.4 | + | + | + | + | | + |
| 2 | 69B.4 | + | | | | | 3+ |
| | RS11$^{CT}$ | + | | + | | | 3+ |
| | RS14 | + | + | + | + | + | + |
| 3 | wE1 | + | + | + | + | + | |
| | wN10 | + | + | + | + | + | |
| | WN16$^{CT}$ | + | + | + | + | + | |
| 4 | 13C.1 | + | + | + | + | | 3+ |
| | 23M.1 | + | + | + | + | | 3+ |
| | 14LN.1 | + | + | + | + | | 4+ |
| | 15LN.1$^{CT}$ | + | + | + | + | | 4+ |
| — | wE2 | + | + | + | + | + | 2+ |
| 5 | 66B.4 | + | + | + | + | + | + |
| | RS17 | + | + | + | + | + | + |
| | AB49 | + | + | + | + | + | |

TABLE 6-continued

Polar Lipid Components of Gram-Positive Alkaliphilic Bacteria

| CLUSTER | STRAIN | PG | DPG | PGP | PI | PE | GL |
|---------|--------|----|----|-----|----|----|-----|
| 6 | RS7 | + | + | + | + |  | 2+ |
|  | RS15 | + | + | + | + |  | 2+ |
| — | 72C.4 | + | + | + | + |  | 3+ |
| — | 80LN.4 | + | + | + | + |  | 3+ |

(PG) phosphatidylglycerol; (DPG) diphosphatidylglycerol; (PGP) phosphatidylglycerolphosphate; (PI) phosphatidylinositol; (PE) phosphatidylethanolamine (ninhydrin positive aminolipid); (GL) unidentified glycolipid(s), α-naphthol positive (the number in the column gives the number of positive spots on the TLC plate).

Isoprenoid Quinones

The isoprenoid or respiratory quinones are characteristic components of the plasma membrane of aerobic bacteria. There are two types; menaquinones and ubiquinones. The value of isoprenoid quinones as taxonomic criteria lies in the variation in the length of the polyprenyl side-chain and the degree of saturation (Collins, M. D. and Jones, D. (1981), supra).

Dry stationary phase bacterial cells were extracted, using a modified procedure of Collins, M. D. (in *Chemical Methods in Bacterial Systematics*, supra, pp. 267–284), in 1:1 (v/v) $CHCl_3:CH_3OH$ at 50° C., for 16 hours. The quinones were examined by reverse phase thin layer chromatography as described by Collins, M. D. (supra).

The results of quinone analyses of representative strains of Gram-positive alkaliphiles are illustrated in Table 7. However, there is no evidence to suggest that quinone composition is of value in the circumscription of the clusters, although the data do serve to confirm the status of these strains as Gram-positive. Furthermore, MK-7 as the major isoprenologue of Bacillus species, including alkaliphilic strains, is also confirmed (Lechevalier, H. and Lechevalier, M. P., supra, p. 881). Many of the novel, Gram-positive alkaliphilic bacteria of the present invention contain shorter molecules, especially MK-4 and MK-6, although no clear pattern emerges.

TABLE 7

Menaquinone Components of Gram-Positive Alkaliphilic Bacteria

| CLUSTER | STRAIN | MENAQUINONE | | | | | | | |
|---------|--------|---|---|---|---|---|---|---|---|
| 1 | 3E.1[CT] | 3 | 4 | | | | | | |
|  | 71C.4 |  | 4 | 5 | $5H_2$ | 6 | | | |
|  | 81LN.1 |  | 4 | | | | 7 | | |
|  | 60E.4 | 3 | 4 | | | | | 8 | |
|  | wE4 |  | 4 | 5 | | | | | |
| 2 | 69B.4 |  | 4 | | | 6 | 7 | | 9 |
|  | RS11[CT] |  |  | | | | 7 | 8 | |
| 3 | wE1 |  |  | | | 6 | 7 | | |
|  | wN10 |  |  | | | 6 | | | |
|  | wN12 |  |  | | | 6 | 7 | | |
|  | WN16[CT] |  | 4 | | | 6 | | | | 11 |
| 4 | 13C.1 |  | 4 | | | 6 | 7 | | 9 |
|  | 23M.1 |  | 4 | | | | | | |
|  | 14LN.1 |  | 4 | | | 6 | 7 | 8 | $8H_2$ | 9 |
|  | 15LN.1[CT] |  |  | 5 | | 6 | 7 | | $8H_2$ | |
| — | wE2 |  |  | | | | 7 | | |
| — | wB3 |  | 4 | 5 | | | | | |
| 5 | 66B.4 |  | 4 | | | 6 | 7 | | |
|  | RS17 |  | 4 | | | | 7 | 8 | |
|  | AB49 |  |  | | | | 7 | | |
| 6 | RS7 |  | 4 | 5 | | | 7 | 8 | |

Fatty Acids

The analysis of fatty acid profiles has had a significant impact on bacterial classification especially in the assignment of genera and species among Gram-positive bacteria and actinomycetes (Kroppenstedt, R. M., in *Chemical Methods in Bacterial Systematics* (eds. M. Goodfellow and D. E. Minnikin), Academic Press; London and Orlando, Fla., (1985), pp. 173–199); Lechevalier, H. and Lechevalier, M. P., supra.

Freeze dried stationary phase cells (200–300 mg) were extracted for 16 hours at 75° C. in toluene:methanol:conc. sulfuric acid (2.5 ml:2.5 ml:0.2 ml) and after cooling, the lipids were partitioned into hexane (twice times 1 ml). Residual acid was removed using $NH_4HCO_3$. Lipid extracts were concentrated under $O_2$-free $N_2$, dissolved in 300 μl hexane and applied to preparative silica gel plates (Merck F254, Type T). The plates were developed in hexane: diethyl ether 85:15 (v/v) and the fatty acid methyl esters scraped off, extracted with hexane and concentrated under a stream of $O_2$-free $N_2$.

The fatty acid methyl esters were dissolved in heptane and analysed by gas chromatography using a Packard model 430 chromatograph equipped with flame ionization detectors. The samples were divided by a sample splitter and analyzed simultaneously over two columns, namely, CP-SIL-88 (Chrompack) (length 50 meter, internal diameter 0.22 mm) and Ultra-2 (Hewlett Packard) (length 50 m, internal diameter 0.20 mm). The carrier gas was nitrogen; the injection temperature 120° C.; temperature gradient 2.5° C. per minute to 240° C. and isothermal at 240° C. for 30 minutes. Fatty acid methyl esters were assigned by reference to known standard mixtures. The identity of some peaks was confirmed by means of gas chromatography-mass spectrometry using a Carlo Erba HRGC 5160 Mega series gas chromatograph equipped with a CP-SIL-88 column (length 50 meter, internal diameter 0.22 mm) with helium as carrier gas and direct injection into the source of a AMD 403 mass spectrometer.

The fatty acid composition of the individual Gram-positive alkaliphilic bacteria is set out in Table 8. Table 9 shows the unique fatty acid profiles of the individual clusters. Clusters 5 and 6 are typical for Bacillus species with a predominance of branched C15:0 and C17:0 fatty acids. In spite of the homgeneity of cluster 4 shown by the numerical taxonomy, fatty acid profiles clearly demonstrate that two subgroups of bacteria (designated 4A and 4B) exist within this cluster. These profiles are typical of some members of the Coryneform-Mycobacterium-Nocardioform (CMN) groups of the actinomycetes (Bennan, P. J., in *Microbial Lioids*, supra, pp 203–298), a designation supported by their characteristic cell habit, and the appearance of dihydromenaquinones. Furthermore, the bright orange-yellow colors of many actinomycetes is caused by the accumulation of carotenoid pigments, often induced by light. Many of these carotenoids are unique and important taxonomically. Further chemotaxonomic markers for these groups include a branched C19:0 fatty acid which is 10-methyloctadecanoic acid (tuberculostearic acid), an important criterion in the classification of the CMN group of bacteria. Branched, unsaturated fatty acids are also found in these bacteria. Branched C20:0 fatty acids, found in Clusters 3 and 4 are components of some Gram-positive cocci. The control bacteria for the coryneform group, namely *Arthrobacter luteus* (now reclassified as *Oerskovia xanthinolytica*) and *Brevibacterium linens* do not associate closely with any of the clusters. However, the known obligate alkaliphiles among the CMN class of bacteria are poorly characterized but are clearly different from the novel Gram-positive alkaliphiles of the present invention.

TABLE 8

Fatty Acid Composition[+] of Gram-Positive Alkaliphiles

| FATTY ACID | Cluster 1 | | Cluster 2 | | Cluster 3 | | | Cluster 4 | | | Cluster 5 | | Cluster 6 | | Unclustered | |
|---|---|---|---|---|---|---|---|---|---|---|---|---|---|---|---|---|
| | 3E.1 | 81LN.4 | 69B.4 | RS11 | wE1 | wN12 | wN16 | 23M.1 | 14LN.1 | 15LN.1 | 66B.4 | AB49 | RS8 | RS16 | wB3 | 72C.4 |
| C11:0 | t | 0.2 | — | — | t | t | — | — | — | — | — | t | — | t | — | — |
| C12:0 | 0.4 | 0.4 | 1.0 | 0.9 | 0.5 | t | 0.2 | 0.2 | 0.4 | 0.7 | 0.5 | t | 0.3 | 0.5 | 1.2 | 1.0 |
| C14:0 | 3.4 | 3.2 | 5.9 | 6.0 | 4.3 | 1.5 | 5.3 | 1.8 | 3.5 | 5.1 | 3.1 | 2.9 | 3.9 | 3.6 | 7.4 | 6.9 |
| C14:0 iso | 0.7 | — | — | — | 0.7 | 0.2 | — | 0.5 | — | — | 1.3 | 0.9 | 0.3 | 0.2 | 0.1 | — |
| C15:0 | 0.5 | 0.2 | 0.4 | 0.5 | 0.4 | 1.1 | 0.4 | 0.2 | 0.9 | 0.4 | 0.6 | 0.6 | 0.5 | 0.3 | 0.5 | 0.4 |
| C15:0 iso | 3.2 | 0.8 | 0.3 | 0.3 | 1.9 | 7.6 | 0.2 | 1.4 | — | 0.2 | 13.1 | 13.2 | 18.9 | 3.1 | 0.5 | 0.4 |
| C15:0 anteiso | 27.6 | 15.2 | 0.6 | 0.1 | 8.2 | 17.5 | 0.1 | 11.2 | — | 0.1 | 22.4 | 13.1 | 6.7 | 10.1 | 3.5 | 1.8 |
| C16:0 | 17.6 | 21.2 | 28.1 | 30.6 | 26.2 | 22.9 | 30.8 | 9.8 | 29.4 | 28.4 | 15.8 | 22.3 | 25.5 | 23.0 | 30.6 | 30.7 |
| C16:0 iso | 5.1 | 0.5 | 0.1 | — | 0.7 | 1.1 | — | 13.0 | — | — | 6.4 | 6.1 | 1.4 | 0.4 | 1.0 | 0.7 |
| C16:1 | — | — | — | — | — | — | — | — | 3.1 | t | — | — | — | — | — | — |
| C16:1 br | — | — | — | — | — | — | — | 1.8 | — | — | — | — | — | — | — | — |
| C17:0 | 0.4 | 0.4 | 0.7 | 0.7 | 0.6 | 1.0 | 0.6 | 3.8 | 3.3 | 0.8 | 0.7 | 0.6 | 0.4 | 0.5 | 0.6 | 0.6 |
| C17:0 iso | 1.4 | 0.6 | — | — | 0.3 | 0.7 | — | 1.6 | — | — | 3.4 | 8.1 | 6.3 | 1.1 | — | — |
| C17:0 anteiso | 14.2 | 13.4 | — | — | 1.2 | 4.7 | — | 40.9 | — | — | 10.4 | 12.3 | 4.1 | 5.4 | 3.1 | 1.4 |
| C17:1 | — | — | — | — | — | — | — | — | 2.6 | — | — | 0.3 | — | — | — | — |
| C18:0 | 12.9 | 22.2 | 31.1 | 31.2 | 28.0 | 28.5 | 30.5 | 6.7 | 18.7 | 30.1 | 11.3 | 10.7 | 16.8 | 28.5 | 25.0 | 28.4 |
| C18:1 cis/trans | 6.6 | 4.4 | 13.9 | 6.3 | 4.9 | 5.2 | 6.6 | 2.7 | 19.9 | 7.6 | 5.5 | 1.9 | 4.1 | 4.7 | 9.3 | 8.7 |
| C18:2 | 1.5 | 0.9 | 6.0 | 2.8 | 1.5* | 2.3* | 3.2* | 1.1* | 0.9* | 4.1* | 1.4 | 0.3 | 0.5 | 0.9 | 5.9* | 5.0* |
| unknown | | | | | | | | 0.5 | | | | | | 0.2 | | |
| C19:0 br | — | — | — | — | — | — | — | — | 3.2 | 0.4 | — | — | — | — | — | — |
| C20:0 | 3.1 | 9.8 | 7.7 | 11.9 | 12.1 | 0.8 | 12.7 | 1.7 | 8.1 | 12.5 | 2.7 | 4.1 | 5.8 | 10.8 | 7.4 | 9.1 |
| C22:0 | 1.5 | 6.2 | 4.2 | 8.2 | 8.2 | 5.1 | 8.8 | 0.9 | 5.7 | 9.0 | 1.6 | 2.7 | 3.8 | 6.8 | 3.9 | 5.5 |
| C23:0 | — | — | — | — | — | — | — | 0.2 | — | — | — | — | 0.3 | — | — | — |
| C24:0 | t | 0.4 | t | 0.6 | 0.5 | — | 0.6 | t | 0.3 | 0.6 | t | 0.2 | 0.2 | 0.3 | — | — | t = trace
br = branched
\* = C18:2 and/or C20:0 br
[+] = as % of total fatty acids

TABLE 9

Fatty Acid Profiles of the Clusters of Gram-Positive Alkaliphiles

| | CLUSTER | | | | | | |
|---|---|---|---|---|---|---|---|
| | 1 | 2 | 3 | 4A | 4B | 5 | 6 |
| Predominant Fatty Acids (>10%) | C15:0 anteiso C16:0 C17:0 anteiso C18:0 | C16:0 C18:0 | C16:0 C18:0 C20:0 | C15:0 anteiso C16:0 C17:0 anteiso | C16:0 C18:0 | C15:0 iso C15:0 anteiso C16:0 C17:0 anteiso C18:0 | C15:0 br C16:0 C18:0 |
| n-saturated | 40–65% | 80–90% | 60–90% | ≈25% | 70–90% | 35–45% | 55–75% |
| n-unsaturated | <10% | 10–20% | <10% | ≈5% | 10–30% | <10% | ≈5% |
| iso | 1–10% | <1% | <10% | ≈15% | <1% | 20–30% | 5–30% |
| anteiso | 30–40% | <1% | 0–20% | ≈50% | <1% | 25–35% | 10–15% |
| total branched | 30–50% | <1% | 0–30% | ≈70% | <5% | 50–60% | 20–40% |
| even carbon no. | 50–70% | >95% | 70–99% | ≈40% | >90% | ≈50% | 60–80% |
| odd carbon no. | 30–50% | <5% | 1–30% | ≈60% | <10% | ≈50% | 20–40% |
| additional markers | | | C20:0 br | C16:1 br C20:0br | C19:0 br C20:0 br | | | br = branched

DNA Base Composition

An important component of a taxonomic study is an analysis of the genetic material—the nucleic acids. The composition of chromosomal DNA is unaffected by the growth conditions of the organism and an appropriate analysis may confirm or refute the taxonomic position of the organism. Chromosomal DNA may be analyzed by the determination of the base composition (G+C mol %) of individual strains. The guanine plus cytosine (G+C mol %) composition is constant for the chromosomal DNA from any given organism. Closely related organisms have similar G+C compositions. However, G+C results must be interpreted within the context of independent taxonomic data since similar G+C mol% of DNA samples from different organisms does not in itself imply biological relatedness.

DNA was extracted from cells grown to exponential phase in Medium A by the chloroform:phenol method and was precipitated with ethanol. Base composition was determined by the thermal denaturation method (Marmur, J. and Doty, P. (1962), J. Mol. Biol., 3, 585–595) on a Phillips model PV8764 spectrophotometer with temperature programming. A second method involved HPLC analysis on a Beckman system gold using a Beckman ultrasphere ODS column and 0.04M potassium dihydrogen phosphate plus acetonitrile (9+1, v/v) as eluent at a flow rate of 1.5 ml/min., after treatment of the DNA with nuclease P1 and alkaline phosphatase.

The results of these analyses are set out in Table 10. These results are consistent with the grouping of the bacteria as defined by the numerical taxonomy analysis. The G+C mol % values for the new alkaliphilic bacteria (clusters 1,3 and 4) cover a range of 29% (34.1–63.5 mol %). However, within these clusters the variation is less than 15 mol %, which confirms that the strains within a cluster are more closely related to each other than to strains outside the cluster. Furthermore, it is evident that the new strains in clusters 1 and 4 with a high G+C content (52.3–63.5 mol %) are clearly different from the known Bacillus strains in clusters 2 (35.0–39.6 mol %), 5 (36.1–42.8 mol %) and 6 (36.5–43.6 mol %). The new strains of cluster 3 (G+C= 34.1–46.3 mol %) are clearly differentiated from the bacilli on the basis of other chemotaxonomic data.

TABLE 10

DNA Base Composition of Gram-Positive Alkaliphilic Bacteria

| | | G + C mol % | | |
|---|---|---|---|---|
| Cluster | Strain | HPLC | $T_M$ | Literature[1] |
| 1 | 3E.1[CT] | 52.3 | | |
| | wE4 | | 63.1 | |
| 2 | RS11[CT] | 35.0 | | 35.2 |
| | RS14 | | | 39.6 |
| | RS13 | | | 37.2 |
| 3 | wE1 | | 49.3 | |
| | wN10 | | 34.1 | |
| | wN12 | 40.1 | 36.6 | |
| | WN16[CT] | 46.0 | 40.2 | |
| 4 | 23M.1 | 63.0 | | |
| | 15LN.1[CT] | 63.5 | | |
| 5 | 66B.4 | 42.1 | | |
| | RS10[CT] | | | 39.5 |
| | RS17 | | | 42.5 |
| | AB49 | | 42.1 | 42.8 |
| | AB42 | | | 36.1 |
| 6 | RS7 | | | 43.2 |
| | RS8[CT] | 39.9 | | 43.6 |
| | RS15 | | | 43.5 |
| | RS16 | | | 36.5 |

[1]Fritze, D., Flossdorf, D. and Claus, D. (1990) Int. J. Systematic Bacteriology, 40, 92–97.

Determination of Representative Strains

The centroid of each individual cluster generated by the $S_G$/UPGMA method was computed using the RGROUPS program in TAXPAK. The centroid of a cluster of points representing real organisms projected into hyperspace represents a hypothetical average organism. The centroid seldom, if ever, represents a real organism. Therefore, the Euclidean distances of each of the members of the cluster from the centroid of the cluster were calculated in order to establish which organism was closest to the hypothetical average organism. The organism closest to the centroid was designated the "centrotype organism" (indicated with the superscript "CT").

The centrotype organism can be thought of as the "Type Strain" which most closely represents the essential and discriminating features of each particular cluster. The centrotype strains are recorded in Table 11.

TABLE 11

Centrotype Strains

| Cluster Number | Number of Strains in Cluster | Mean Euclidean Distance of Strains from Centroid | Standard Deviation | Centrotype Strain | Euclidean Distance from Centroid |
|---|---|---|---|---|---|
| 1 | 5 | 6.24 | 0.65 | 3E.1 | 4.45 |
| 2 | 5 | 6.02 | 0.23 | RS11 | 4.53 |
| 3 | 4 | 6.81 | 0.96 | wN16 | 4.26 |
| 4 | 4 | 6.40 | 0.57 | 15LN.1 | 4.40 |
| 5 | 6 | 6.44 | 0.27 | RS10 | 5.01 |
| 6 | 4 | 6.50 | 0.72 | RS8 | 4.06 |

A description of each of the centrotype organisms from the clusters containing the novel bacteria has been made so as to be able to distinguish these organisms from all other bacteria previously known and described. In addition, the minimum number of discriminatory tests to define each cluster has been computed so that it may be clearly seen that the clusters containing these novel bacteria can be easily distinguished from each other and from all other known bacteria.

Description of Centrotype Strains
Strain 3E.1$^{CT}$ (Cluster 1)

An aerobic, Gram-positive coccoid bacterium. The cells are almost spherical, 0.5–1.5 μm, usually in pairs or occasionally tetrads, forming short chains of up to 6 cells, or in irregular clusters.

Motility not observed.

Obligate alkaliphile, grows optimally at about pH 10.

On alkaline-agar, (Medium A) forms opaque, matte orange-colored colonies. The color development is influenced by light, beginning as cream developing through yellow to orange. The colonies are circular, convex, entire, 1–2 mm in diameter.

In alkaline-broth (Medium A), growth (37° C.) is moderate, evenly turbid, with the formation of a sediment but no surface pellicle.

Optimum temperature for growth is about 30° C. Grows slowly at 15° C. and 40° C. No growth at 45° C.
KOH test: negative
Aminopeptidase test: negative
Oxidase reaction: negative
Catalase reaction: positive
NaCl tolerance: 0% to 12%. No growth at 15%.
Hydrolysis of Gelatin: positive
Hydrolysis of Starch: weak positive.
Major polar lipid components: phosphatidylglycerol, diphosphatidylglycerol, phosphatidylglycerolphosphate. Three glycolipid (α-naphthol positive) components present.
Major menaquinones: MK-3, MK-4.
Major fatty acids: C15:0 anteiso, C16:0, C17:0 anteiso, C18:0.
G+C: 52.3 mol % (HPLC)

Chemoorganotroph. Grows on complex substrates such as yeast extract and peptones. Growth on simple sugars and organic acids very restricted. Growth is stimulated by glucose, acetate, some amino acids and pyrimidine nucleotides.

Strain wN16$^{CT}$ (Cluster 3)

An aerobic, Gram-positive bacterium. The cells are short, thick, slightly irregular rods, 1.5–2.5 μm×0.75–1.0 μm, occuring singly or in pairs, sometimes in short chains of up to 4 cells.

No spores observed. Motility not observed.

Obligate alkaliphile; no growth below pH 8.

On alkaline-agar, (Medium A) forms smooth, cream-yellow colored colonies. The colonies are small, about 1 mm in diameter, circular, entire and convex.

In alkaline-broth (Medium A), growth (37° C.) is moderate, evenly turbid, forming a sediment but no surface pellicle.

Grows well between 20° C. and 40° C. Grows slowly at 10° C.; no growth at 45° C.
KOH test: negative
Aminopeptidase test: negative
Oxidase reaction: negative
Catalase reaction: negative
NaCl tolerance: 0% to 10%.
Hydrolysis of Gelatin: positive
Hydrolysis of Starch: positive.
Major polar lipid components: phosphatidylglycerol, diphosphatidylglycerol, phosphatidylglycerolphosphate, phosphatidylinositol, phosphatidylethanolamine.
Major menaquinones: MK-4, MK-6, MK-11.
Major fatty acids: C16:0, C18:0, C20:0 (fatty acids with even carbon numbers comprise >95%, branched fatty acids <1%).
G+C: 40.2 mol % (T$_M$)–46.0 mol % (HPLC)

Chemoorganotroph. Grows on complex substrates such as yeast extract, a range of sugars, amino- and organic acids.

Strain 15LN.1$^{CT}$ (Cluster 4)

An aerobic, Gram-positive bacterium. The cells are initially irregular, spherical or elongated, sometimes wedge-shaped, 1.5–2.0 μm×0.75–1 μm, developing into short, thick, slightly curved rods, 1–3 μm×0.5–1 μm. The cells often occur in pairs. Due to the characteristic snapping form of cell division, the cells are frequently found at an angle forming a V-shape, or in clusters of cells with a pallisade appearance.

No spores observed. No motility observed.

Obligate alkaliphile; no growth below pH 7.5, optimum pH≈9–10.

On alkaline-agar, (Medium A) forms brightly colored, smooth, glistening colonies, initially orange developing into red. Color development is influenced by light. The colonies are circular, convex, entire, opaque, 1–2 mm in diameter.

In alkaline-broth (Medium A), growth (37° C.) is slight to moderate, flocculent, with the formation of sediment and a surface ring or pellicle.

Grows well between 20° C. and 40° C. Grows slowly at 45° C and 10° C. No growth at 50° C.
KOH test: negative
Aminopeptidase test: negative
Oxidase reaction: negative
Catalase reaction: positive
NaCl tolerance: 0% to 8%.
Hydrolysis of Gelatin: negative
Hydrolysis of Starch: positive.
Major polar lipid components: phosphatidylglycerol, diphosphatidylglycerol, phosphatidylglycerolphosphate, phosphatidylinositol. Four glycolipid (α-naphthol positive) components present.
Major menaquinones: MK-5, MK-6, MK-7, MK-8(H$_2$)
Major fatty acids: C16:0, C18:0, C20:0 (fatty acids with even carbon numbers comprise >95%, branched fatty acids <1%).
G+C: 63.5 mol % (HPLC)

Chemoorganotroph. Grows on complex substrates such as yeast extract and peptones. Growth on simple sugars very restricted. Growth is stimulated by amino acids and fatty acids.

Non-clustering Strains

The strains which do not fall into the clusters defined here are also novel bacteria not previously known or described. These strains, coded wE2, wB3, 72C.4, 79LN.4 and 80LN.4, may represent rarer varieties of alkaliphilic bacteria. Some of these strains, such as wE2 and wB3 may represent intermediate forms, falling between closely related (and closely orientated in hyperspace) clusters as defined here. The other strains, 72C.4, 79LN.4 and 80LN.4, are probably members of clusters of bacteria representing new genera or species at present not defined. A description of these "non-clustering" strains has been made so as to be able to distinguish these organisms from all other bacteria previously known and described.

Strain wE2

An aerobic, Gram-positive bacterium. The cells are irregular; mainly oval coccoid cells, 1–2 μm×0.5–1 μm, or very short rods, occasionally in pairs, or slightly curved short rods. Due to the characteristic snapping form of cell division, the cells are frequently found at an angle forming a V-shape.

No spores observed. No motility observed.

Obligate alkaliphile; no growth below pH 8.

On alkaline-agar, (Medium A) forms opaque, orange colored, punctiform or circular colonies, with a convex or domed elevation and entire margin, up to 1 mm in diameter.

In alkaline-broth, (Medium A) growth (37° C.) is slow, slight to moderate, flocculent turbidity, with the formation of a sediment and surface ring.

Temperature: grows optimally at above 30° C., slowly at 10° C. No growth at 40° C.

KOH test:negative
Aminopeptidase test: negative
Oxidase reaction: negative
Catalase reaction: positive
NaCl tolerance: 0% to 10%. No growth at 12%.
Hydrolysis of Gelatin: negative
Hydrolysis of Starch: negative
Major polar lipid components: phosphatidylglycerol, diphosphatidylglycerol, phosphatidylglycerolphosphate, phosphatidylinositol, phosphatidylethanolamine. Two glycolipids (α-naphthol positive) components present.
Major menaquinones: MK-7

Chemoorganotroph. Grows on complex substrates such as yeast extract, peptones and carbohydrates (dextrin). Growth is stimulated by a variety of sugars, organic-, fatty- and amino-acids.

Strain wE2 appears to be an intermediate form related to Cluster 4.

Strain wB3

An aerobic, Gram-positive bacterium. The cells are short, straight or slightly curved rods, 1–2.5 μm×0.5 μm, sometimes in pairs. Due to the characteristic snapping form of cell division, the cells are frequently found at an angle forming a V-shape.

Motility not observed. No spores observed.

Obligate alkaliphile; no growth below pH 8. On alkaline-agar, (Medium A) forms opaque yellow/ochre, circular, convex, entire colonies, 2 mm in diameter.

In alkaline-broth, (Medium A) growth (37° C.) is slight to moderate with an even turbidity and the formation of a sediment, but no surface pellicle.

Temperature range for growth: 10° C. to 40° C. No growth at 45° C.

KOH test: negative
Aminopeptidase test: negative
Oxidase reaction: negative
Catalase reaction: positive
NaCl tolerance: 0% to 12%. No growth at 15%.
Hydrolysis of Gelatin: positive
Hydrolysis of Starch: negative
Major menaquinones: MK-4, MK-5.
Major fatty acids: C16:0, C18:0 (fatty acids with even carbon numbers >90%, branched fatty acids <10%).

Chemoorganotroph. Grows on complex substrates such as yeast extract. Growth on simple substrates (sugars, etc.) very restricted. Growth is stimulated by acetate and glucose.

Strain wB3 appears to be an intermediate form related to Cluster 1.

Strain 79LN.4

An aerobic, motile, Gram-positive bacterium. The cells are straight or slightly curved rods, 1.5–5 μm×0.5–1 μm, often in pairs, sometimes in short chains of 2 to 4 cells.

No spores observed. Motility not observed.

Obligate alkaliphile, no growth below pH 7.5.

On alkaline-agar, (Medium A) forms opaque, cream colored colonies, 2 mm in diameter. The colonies are circular, umbonate in elevation, with an entire margin becoming undulate with age.

In alkaline-broth, (Medium A) growth (37° C.) is moderate to heavy, evenly turbid, with the formation of a sediment and eventually a surface ring.

Temperature range: grows well at 20° C. to 40° C. Grows slowly at 10° C. and 45° C. No growth at 50° C.

KOH test:negative
Aminopeptidase test: negative
Oxidase reaction: weak positive
Catalase reaction: positive
NaCl tolerance: 0% to 15%
Hydrolysis of Gelatin: positive
Hydrolysis of Starch: positive Chemoorganotroph. Grows well on complex substrates, simple sugars, organic-, amino- and fatty acids, and pyrimidine nucleotides.

Strain 72C.4

An aerobic, Gram-positive bacterium. The cells appear to have a distinct coccus-rod development cycle. Initially the cells are spherical or irregular coccobacillery in form which develop into short rods, 1–2.5 μm×0.5–0.75 μm. Eventually some longer forms, 3–4 μm×1 μm appear. The cells occur occasionally in pairs. Due to the characteristic snapping form of cell division, the cells are frequently found at an angle forming a V-shape.

No motility observed. No spores observed.

Obligate alkaliphile; no growth below pH 8.

On alkaline-agar, (Medium A) forms circular, convex, entire, opaque colonies, 1–2 mm in diameter. The colony color is initially orange developing with age and the influence of light into a deep salmon pink.

In alkaline-broth, (Medium A) growth (37° C.) is moderate, evenly turbid, with the formation of a sediment but no surface pellicle.

Temperature range: grows well at 20° C. to 37° C. Grows slowly at 10° C. No growth at 40° C.

KOH test: negative
Aminopeptidase test: positive
oxidase reaction: negative
Catalase reaction: positive
NaCl tolerance: 0% to 12%
Hydrolysis of Gelatin: positive
Hydrolysis of Starch: negative
Major polar lipid components: phosphatidylglycerol, diphosphatidylglycerol, phosphatidylglycerolphosphate, phosphatidylinositol. Three glycolipid (α-naphthol positive) components present.

Major fatty acids: C16:0, C18:0 (fatty acids with even carbon numbers >95%, branched fatty acids <5%).

Chemoorganotroph. Grows well on complex substrates (e.g. yeast extract) and a variety of sugars, organic acids and amino acids.

Strain 80LN.4

An aerobic, Gram-positive bacterium. The cells are nearly spherical or coccobacillery in form, developing into very short rods, 1–2 μm×0.5–0.75 μm. Occasionally longer forms occur. The cells occur occasionally in pairs.

No motility observed. No spores observed.

Obligate alkaliphile, no growth at pH 8.

On alkaline-agar, (Medium A) forms circular, convex to umbonate, entire, opaque colonies, 1–2 mm in diameter. The colony color is initially orange developing with age and the influence of light into a deep salmon pink.

In alkaline-broth, (Medium A) growth (37° C.) is moderate, evenly turbid, with the formation of sediment and surface pellicle.

Temperature range: grows well at 20° C. to 37° C. Grows slowly at 10° C. No growth at 40° C.

KOH test: negative

Aminopeptidase test: positive

Oxidase reaction: negative

Catalase reaction: positive

NaCl tolerance: 0% to 12%. Grows weakly at 15%.

Hydrolysis of Gelatin: positive

Hydrolysis of Starch: negative

Major polar lipid components: phosphatidylglycerol, diphosphatidylglycerol, phosphatidylglycerolphosphate, phosphatidylinositol. Three glycolipid (α-naphthol positive) components present.

Chemoorganotroph. Grows well on complex substrates (e.g. yeast extract) and a variety of sugars, organic acids and amino acids.

Cluster Definition by the Calculation of the Minimum Number of Discriminatory Tests, and the Construction of a Probability Matrix for the Identification of Gram-positive Alkaliphiles One of the purposes of a numerical classification study is to use the phenetic data, which define the clusters at a selected similarity level, for the assignment or identification of unknown strains. The classification test data can be used to determine the minimum set of tests which are required to define the clusters at the 79% ($S_G$) similarity level, and to identify those characters which are most diagnostic (predictive) for the individual clusters. In other words, the minimum number of tests which are required to assign an unknown organism to a pre-determined cluster with a high degree of predictability.

From the minimum discriminatory tests, a probability matrix can be constructed for the identification of unknown strains. The analysis is achieved by using a combination of the CHARSEP and DIACHAR programs in TAXPAK, supplemented by the MCHOICE program (not on TAXPAK, but available by Data-Mail from the University of Leicester, U.K.). An evaluation of the identification matrix is provided by using the MOSTTYP, OVERMAT and MATIDEN programs. Practical examples of the use of these programs for the probabilistic identification of bacteria have been published by Williams, S. T., et al., (1983), Journal of General Microbiology, 129, 1815–1830; and Priest, F. G. and Alexander, B., (1988), Journal of General Microbiology, 134, 3011–3018; ibid, (1990), 136, 367–376.

A "nxt" table was constructed using the two-state characters from the test data. In other words, using characters 6 to 11 and 14 to 200 (Appendix C) scored in binary notation (positive=1, negative=0).

The data matrix is first examined using the CHARSEP program which calculates separation indices and thus the diagnostic value of the individual characters for discriminating between the clusters. Character-states (tests) with a VSP index [(4 times variance) times strain potential] greater than 25% (Sneath, P. H. A., (1979), Computers and Geosciences, 5, 349–357) are accepted, characters with a low diagnostic value (VSP <25%) are rejected. A preference is made for characters with the highest VSP indices, provided that the criteria in the DIACHAR and MCHOICE programs are also met. In this example, 63 tests have a VSP index >25%, and 16 of the 32 characters finally chosen have a VSP index >50% (Table 12).

The data matrix is next re-examined by means of the DIACHAR program, which determines the most diagnostic character states of each of the clusters. The number of character states was set at 12. This result allows the choice of mutually exclusive character states between the clusters. As many of these tests as possible are retained in the final identification matrix of minimum discriminatory tests; in this example between 4 and 10 diagnostic characters per cluster. The remaining, unused tests are also noted and may be applied as additional tests for the confirmation of identification (Table 13).

The MCHOICE program ranks the tests in groups which can be displayed in the form of a dendrogram using the MDEND sub-routine. The groups identify tests with similar discriminatory value, thus allowing the rejection of tests which fail to make a significant discrimination as well as allowing choices to be made between tests of equal or very similar diagnostic value.

Table 14 shows the set of 32 tests which is the minimum number required to define the clusters and which can be used for the assignment of unknown strains. In addition, Table 14 shows the identification matrix which consists of the percentage of positive characters which define the clusters on the basis of the 32 minimum discriminatory tests. This is computed by the IDMAT program.

TABLE 12

Separation Values of Characters used for the Minimum Discriminatory Tests

| CHARACTER | VSP Index |
|---|---|
| [10] Gelatin | 30.6 |
| [14] Fumarate | 35.4 |
| [15] Fructose | 35.2 |
| [19] Galactose | 34.8 |
| [24] N-acetylglucosamine | 58.1 |
| [27] D-saccharose | 74.1 |
| [28] Maltose | 70.7 |
| [32] Acetate | 56.8 |
| [36] D-glucose | 63.1 |
| [37] Salicin | 51.3 |
| [38] D-melibiose | 45.0 |
| [42] Propionate | 72.4 |
| [44] Valerate | 31.7 |
| [48] Glycogen | 85.3 |
| [50] L-serine | 38.1 |
| [63] Chymotrypsin | 44.4 |
| [70] β-glucosidase | 67.1 |
| [74] Serine | 58.6 |
| [77] Arginine | 65.3 |
| [80] Methionine | 54.0 |
| [90] Penicillin G | 55.9 |
| [94] Methicillin | 56.5 |
| [96] Streptomycin | 28.5 |

TABLE 12-continued

Separation Values of Characters used for the Minimum Discriminatory Tests

| CHARACTER | VSP Index |
|---|---|
| [97] Tetracyclin | 51.8 |
| [105] Bacitracin | 32.8 |
| [112] N-acetyl-D-glucosamine | 32.8 |
| [116] Cellobiose | 45.0 |
| [137] Turanose | 55.5 |
| [139] Methyl pyruvate | 41.1 |
| [140] Mono-methylsuccinate | 39.1 |
| [192] Thymidine | 34.9 |
| [197] Glycerol | 34.0 |

TABLE 13

Discriminatory Tests for Each of the Six Clusters ($S_G$)

| Positive | | Negative | |
|---|---|---|---|
| Cluster 1: matte orange colored circular colonies; coccoid cells. | | | |
| [10] Gelatin hydrolysis | | [24] N-acetylglucosamine | |
| [90] Penicillin G | | [27] D-saccharose | |
| [94] Methicillin | | [37] Salicin | |
| [105] Bacitracin | | [38] D-melibiose | |
| | | [42] Propionate | |
| | | [48] Glycogen | |
| | | [52] 3-hydroxybutyrate | |
| | | [74] Serine | |
| | | [77] Arginine | |
| | | [80] Methionine | |
| | | [83] Valine | |
| | | [116] Cellobiose | |
| Cluster 2: | | | |
| [10] Gelatin hydrolysis | | [24] N-acetylglucosamine | |
| [15] Fructose | | [42] Propionate | |
| [28] Maltose | | [44] Valerate | |
| [37] Salicin | | [50] L-serine | |
| [70] β-glucosidase | | [89] Trimethoprim | |
| [74] Serine | | [123] m-inositol | |
| [80] Methionine | | [197] Glycerol | |
| [86] Ampicillin | | | |
| [94] Methicillin | | | |
| [96] Streptomycin | | | |
| [105] Bacitracin | | | |
| [137] Turanose | | | |
| Cluster 3: yellow colonies; rod-shaped cells in chains. | | | |
| [10] Gelatin hydrolysis | | [28] Maltose | |
| [19] Galactose | | [32] Acetate | |
| [70] β-glucosidase | | [36] D-glucose | |
| [77] Arginine | | [38] D-melibiose | |
| [105] Bacitracin | | [42] Propionate | |
| [112] N-acetyl-D-glucosamine | | [44] Valerate | |
| [116] Cellobiose | | [48] Glycogen | |
| [190] Inosine | | [74] Serine | |
| [191] Uridine | | [86] Ampicillin | |
| | | [90] Penicillin G | |
| | | [94] Methicillin | |
| | | [97] Tetracyclin | |
| | | [139] Methyl pyruvate | |
| | | [140] Mono-methylsuccinate | |
| | | [155] α-ketobutyric acid | |
| Cluster 4: glistening bright orange/red colonies; cells coccobacillery | | | |
| [77] Arginine | | [10] Gelatin hydrolysis | |
| [80] Methionine | | [14] Fumarate | |
| [82] Glycine | | [15] Fructose | |
| [83] Valine | | [19] Galactose | |
| [94] Methicillin | | [27] D-saccharose | |
| [97] Tetracyclin | | [38] D-melibiose | |
| [105] Bacitracin | | [48] Glycogen | |

TABLE 13-continued

Discriminatory Tests for Each of the Six Clusters ($S_G$)

| Positive | | Negative | |
|---|---|---|---|
| [106] α-cyclodextrin | | [50] L-serine | |
| [109] Tween 40 | | [70] β-glucosidase | |
| [139] Methyl pyruvate | | [112] N-acetyl-D-glucosamine | |
| [140] Mono-methylsuccinate | | [116] Cellobiose | |
| [151] β-hydroxybutyric acid | | [134] D-sorbitol | |
| [165] Bromo-succinic acid | | [136] D-trehalose | |
| | | [137] Turanose | |
| Cluster 5: beige or dull cream colonies; straight rod-shaped cells. | | | |
| [10] Gelatin hydrolysis | | [140] Mono-methylsuccinate | |
| [24] N-acetylglucosamine | | [157] α-ketovaleric acid | |
| [27] D-saccharose | | | |
| [28] Maltose | | | |
| [32] Acetate | | | |
| [36] D-glucose | | | |
| [48] Glycogen | | | |
| [63] Chymotrypsin | | | |
| [86] Ampicillin | | | |
| [94] Methicillin | | | |
| [97] Tetracyclin | | | |
| [137] Turanose | | | |
| Cluster 6: cream colonies; straight rod-shaped cells. | | | |
| [10] Gelatin hydrolysis | | [19] Galactose | |
| [15] Fructose | | [63] Chymotrypsin | |
| [24] N-acetylglucosamine | | [74] Serine | |
| [27] D-saccharose | | [75] Proline | |
| [28] Maltose | | [77] Arginine | |
| [32] Acetate | | [96] Streptomycin | |
| [36] D-glucose | | [99] Oleandomycin | |
| [37] Salicin | | [105] Bacitracin | |
| [38] D-melibiose | | [116] Cellobiose | |
| [42] Propionate | | [140] Mono-methylsuccinate | |
| [45] Citrate | | [192] Thymidine | |
| [48] Glycogen | | | |
| [50] L-serine | | | |
| [66] α-galactosidase | | | |
| [67] β-galactosidase | | | |
| [68] β-glucuronidase | | | |
| [70] β-glucosidase | | | |
| [123] m-inositol | | | |
| [137] Turanose | | | |
| [197] Glycerol | | | |

Note:
The numbers in square brackets proceeding the character state refers to the character states and unit tests in Appendices B and C.

TABLE 14

Identification Matrix: Percentage of Positive Discriminatory Characters which Define the Clusters of Gram-Positive Alkaliphilic Bacteria at the 79% Level ($S_G$)

| TEST | | CLUSTER | | | | | |
|---|---|---|---|---|---|---|---|
| | | 1 | 2 | 3 | 4 | 5 | 6 |
| [10] | Gelatin | 100 | 100 | 100 | 0 | 100 | 100 |
| [14] | Fumarate | 20 | 25 | 75 | 0 | 83 | 50 |
| [15] | Fructose | 60 | 100 | 75 | 0 | 83 | 100 |
| [19] | Galactose | 20 | 25 | 100 | 0 | 17 | 0 |
| [24] | N-acetylglucosamine | 0 | 0 | 50 | 25 | 100 | 100 |
| [27] | D-saccharose | 0 | 75 | 25 | 0 | 100 | 100 |
| [28] | Maltose | 20 | 100 | 0 | 25 | 100 | 100 |
| [32] | Acetate | 20 | 25 | 0 | 75 | 100 | 100 |
| [36] | D-glucose | 20 | 75 | 0 | 25 | 100 | 100 |
| [37] | Salicin | 0 | 100 | 50 | 25 | 67 | 100 |
| [38] | D-melibiose | 0 | 50 | 0 | 0 | 50 | 100 |
| [42] | Propionate | 0 | 0 | 0 | 75 | 83 | 100 |
| [44] | Valerate | 20 | 0 | 0 | 50 | 83 | 50 |
| [48] | Glycogen | 0 | 75 | 0 | 0 | 100 | 100 |
| [50] | L-serine | 40 | 0 | 25 | 0 | 17 | 100 |

TABLE 14-continued

Identification Matrix: Percentage of Positive Discriminatory
Characters which Define the Clusters of Gram-Positive
Alkaliphilic Bacteria at the 79% Level ($S_G$)

| TEST | | CLUSTER | | | | | |
|---|---|---|---|---|---|---|---|
| | | 1 | 2 | 3 | 4 | 5 | 6 |
| [63] | Chymotrypsin | 40 | 25 | 75 | 25 | 100 | 0 |
| [70] | β-glucosidase | 20 | 100 | 100 | 0 | 33 | 100 |
| [74] | Serine | 0 | 100 | 0 | 75 | 50 | 0 |
| [77] | Arginine | 0 | 50 | 100 | 100 | 33 | 0 |
| [80] | Methionine | 0 | 100 | nc | 100 | 33 | 25 |
| [90] | Penicillin G | 100 | 75 | 0 | 50 | 83 | 0 |
| [94] | Methicillin | 100 | 100 | 0 | 100 | 100 | 25 |
| [96] | Streptomycin | 40 | 100 | 50 | 75 | 67 | 0 |
| [97] | Tetracyclin | 80 | 75 | 0 | 100 | 100 | 25 |
| [105] | Bacitracin | 100 | 100 | 100 | 100 | 83 | 0 |
| [112] | N-acetyl-D-glucosamine | 40 | 25 | 100 | 0 | 50 | 50 |
| [116] | Cellobiose | 0 | 50 | 100 | 0 | 50 | 0 |
| [137] | Turanose | 40 | 100 | 25 | 0 | 100 | 100 |
| [139] | Methyl pyruvate | 60 | 75 | 0 | 100 | 33 | 75 |
| [140] | Mono-methylsuccinate | 40 | 25 | 0 | 100 | 0 | 0 |
| [192] | Thymidine | 80 | 25 | 50 | 50 | 83 | 0 |
| [197] | Glycerol | 80 | 0 | 50 | 25 | 33 | 100 | nc = not computed

Evaluation of the Discriminatory Tests and
Assessment of the Reliability of Identification The evaluation of the discriminatory tests has two aspects. Firstly, the validity of the tests can be analysed using practical examples, which can be further evaluated using statistical theory, or the tests can be directly subjected to theoretical assessment using statistical methods.

Illustration 1

A Practical Evaluation of the Discriminatory Tests

Figure 4:
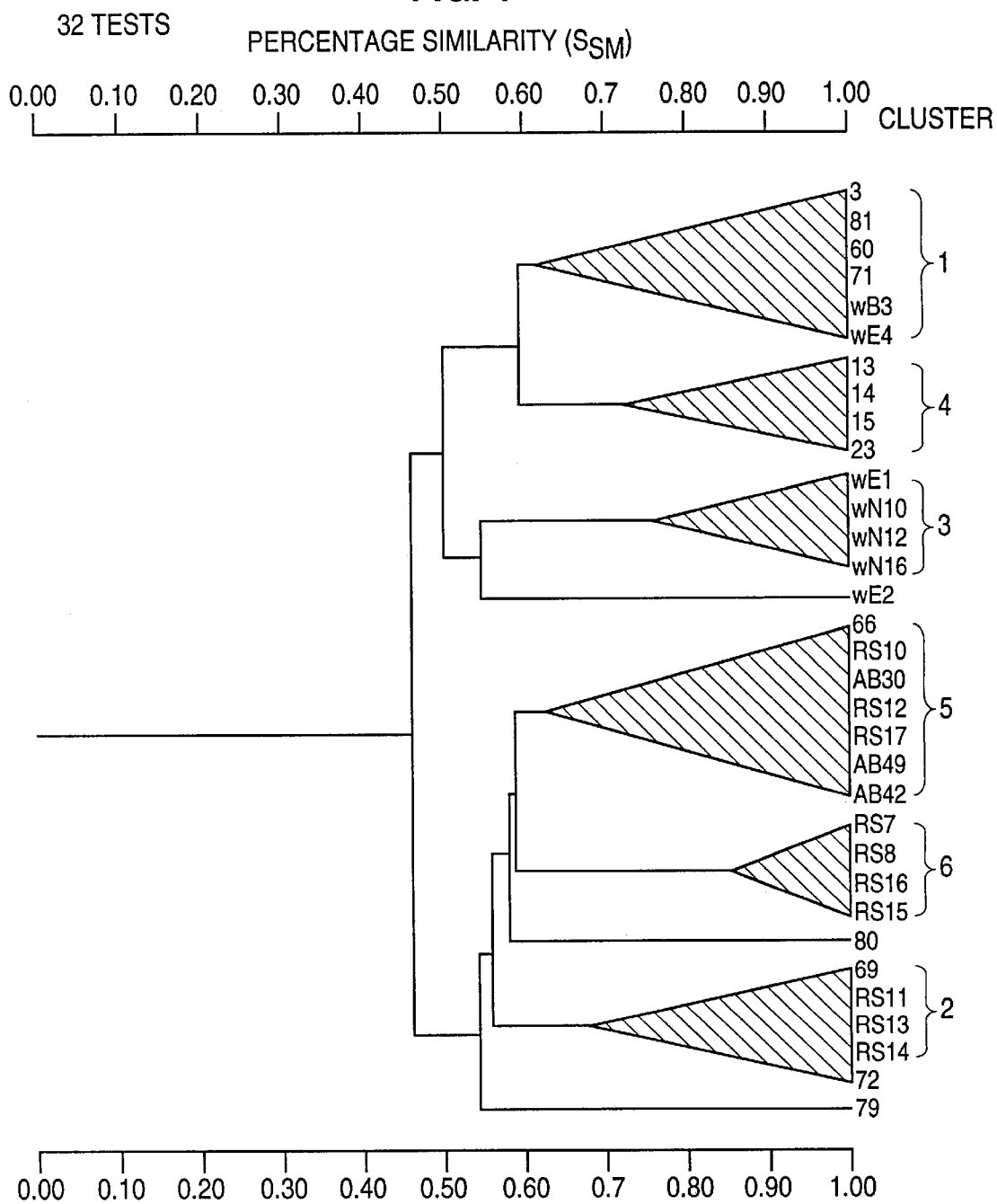
FIG. 4. Simplified dendrogram obtained with the $S_{SM}$ coefficient and Unweighted Average Linkage procedure using the derived minimum discriminatory tests.

Many workers assess the accuracy of the discriminatory tests only by redetermining the character states of selected cluster representatives. This approach has been used here for the centrotype strains (see below). A far more stringent approach which is seldom applied, is to examine all the strains which were used in the original numerical taxonomic analysis. When subjected to cluster analysis using only the data acquired from the derived set of minimum discriminatory tests, the reconstructed dendrogram can be compared with the original. Using only the 32 discriminatory tests previously described (Table 14), the data (two-state, binary form) for all 20 of the new Gram-positive alkaliphilic bacteria and 13 known alkaliphilic Bacillus species isolated by Japanese workers, were subjected to cluster analysis by the $S_G$/UPGMA method (equivalent in this case to the $S_{SM}$/UPGMA method). The reconstructed dendrogram is reproduced in FIG. 4. This reconstructed dendrogram compares very favorably with the original dendrograms (FIGS. 1 and 2).

Although there has been some rearrangement of position of the clusters, their composition is largely unchanged and there is a clear separation between the clusters of novel alkaliphilic bacteria of the present invention and the alkaliphilic Bacillus species.

This evidence, together with the statistical data provided by the numerical taxonomic analysis and the chemotaxonomic data, indicates a robust classification which identifies three major groups of novel Gram-positive alkaliphilic bacteria.

Illustration 2

A Theoretical Evaluation of the Discriminatory Tests

The significance of the apparent clear cluster separation obtained in Illustration 1 (above) can be evaluated using the OVERMAT program which assesses cluster overlap between taxa in an identification matrix. This program examines the matrix constructed from the percentage positive values for the selected character states against a critical overlap value by considering the clusters defined by the coordinates of the centroid and cluster radius (twice root mean square of the distances of the strains of the cluster from the centroid). If there is significant overlap between the clusters, unknown strains may not identify with sufficient confidence to any one of them (Sneath, P. H. A. and Sokal, R. R., supra, p. 394–400). At a chosen critical overlap value of 2.5% (which is a more stringent condition than is used by most workers: see Priest, F. G. and Alexander, B., (1988), supra; and Williams, S. T. et al. (supra), there was no significant overlap (99% confidence level) between most of the clusters (Table 15). Even at a 1% critical overlap value there was no significant cluster overlap (Table 16) except between Cluster 2 and Cluster 5, but since these both represent Bacillus strains this is not considered to have any practical significance for the correct identification of the new Gram-positive alkaliphiles.

TABLE 15

Percentage Probability that Cluster Overlap is <2.5%

| CLUSTER | 1 | 2 | 3 | 4 | 5 | 6 |
|---|---|---|---|---|---|---|
| 1 | | | | | | |
| 2 | 99 | | | | | |
| 3 | 99 | 99 | | | | |
| 4 | 95 | 99 | 99 | | | |
| 5 | 99 | 95 | 99 | 99 | | |
| 6 | 99 | 99 | 99 | 99 | 99 | |

TABLE 16

Percentage Probability that Cluster Overlap is <1%

| CLUSTER | 1 | 2 | 3 | 4 | 5 | 6 |
|---|---|---|---|---|---|---|
| 1 | | | | | | |
| 2 | 95 | | | | | |
| 3 | 95 | 95 | | | | |
| 4 | 90 | 95 | 99 | | | |
| 5 | 95 | <90 | 99 | 99 | | |
| 6 | 99 | 95 | 99 | 99 | 95 | |

Illustration 3

A Theoretical Assessment of the Reliability of Identification

The hypothetical median organism (HMO) is another estimate of the "average" organism in a cluster (Sneath, P. H. A. and Sokal, R. R., supra, pp. 195, et seq.). A HMO is not a real strain but a hypothetical organism possessing the most common state for each character. The MOSTTYP program calculates HMO's for each cluster in the identification matrix and then attempts to identify them. In other words, MOSTTYP is a program to evaluate an identification matrix by calculating identification scores of the most typical strains against the clusters. A good identification matrix should give a high probability of a HMO being reassigned to its own cluster. The results of this analysis were very satisfactory. Each HMO was reassigned to its original cluster with Willcox probabilities of 1.000 (Willcox, W. R. et al., (1973) Journal of General Microbiology, 77, 317–330). The taxonomic distances were all low and the standard errors of the taxonomic distance were all negative, indicating that the HMO's were all closer to the centroid of the cluster than the average for the cluster (Table 17).

TABLE 17

Identification Scores for the Hypothetical Median Organism of each cluster provided by the MOSTTYP Program

| CLUSTER | Identification Score | | |
| --- | --- | --- | --- |
| | Willcox Probability | Taxonomic Distance | Standard Error of Taxonomic Distance |
| 1 | 1.000 | 0.229 | −3.086 |
| 2 | 1.000 | 0.221 | −3.200 |
| 3 | 1.000 | 0.242 | −2.288 |
| 4 | 1.000 | 0.207 | −3.090 |
| 5 | 1.000 | 0.251 | −2.701 |
| 6 | 1.000 | 0.177 | −2.690 |

Illustration 4

A Practical Evaluation of Identification Score

Identification of strains using the minimum set of discriminatory tests is achieved using the MATIDEN program in TAXPAK. The program compares presence-absence data for an unknown strain against each cluster in turn in an identification matrix of percentage positive characters. Identification coefficients are computed, namely Willcox probability, Taxonomic Distance and the Standard Error of the Taxonomic Distance. The results are displayed, showing the identification scores to the best cluster and to the two next best alternative clusters. Additionally, the atypical results ("characters against") are recorded. In an analysis using data from real strains, the centrotypes were reassigned to their original clusters with Willcox probabilities of 1.000 (Table 18). The taxonomic distances were low, generally in the same range as the HMO's. The standard errors of the taxonomic distance were all negative indicating that the centrotypes were closer to the centroid of the cluster than the average for the cluster. The exception was Bacillus reference strain RS10 but this was well within the acceptable limits of +3.0 (Sneath, P. H. A. (1979), pp. 195–213).

TABLE 18

Identification Scores for the Centrotype Organisms of Each Cluster Provided by the MATIDEN Program

| Cluster | Strain | Assigned to Cluster | Identification Score | | |
| --- | --- | --- | --- | --- | --- |
| | | | Willcox Probability | Taxonomic Distance (D) | Standard Error of D |
| 1 | 3E.1$^{CT}$ | 1 | 1.000 | 0.289 | −1.088 |
| 2 | RS11$^{CT}$ | 2 | 1.000 | 0.273 | −1.584 |
| 3 | wN16$^{CT}$ | 3 | 1.000 | 0.229 | −1.767 |
| 4 | 15LN.1$^{CT}$ | 4 | 1.000 | 0.217 | −0.519 |
| 5 | RS10$^{CT}$ | 5 | 1.000 | 0.421 | +1.678 |
| 6 | RS8$^{CT}$ | 6 | 1.000 | 0.221 | −2.468 |

Illustration 5

Identification of an Unknown Isolate

The identification matrix was assessed for the ability to assign an unknown Gram-positive alkaliphile to the clusters defined herein. The criteria for a successful identification were:

(a) a bacterium isolated from a similar habitat to, but geographically separate from, the East African soda lakes;

(b) a Willcox probability greater than 0.95 and low values for taxonomic distance and its standard error (<3);

(c) an identification score to the best cluster significantly better than those against the two next best alternatives;

(d) "characters against" the best cluster should be zero or few in number.

An unknown microorganism may be examined using the minimum tests listed in Table 14. The character states are determined and identification scores obtained using the MATIDEN program. This program compares the character states of the unknown with the identification matrix determined for all of the predetermined clusters, computes the best match and assigns the unknown to the most appropriate cluster.

A Willcox probability is calculated to determine the acceptability of identification. Willcox probabilities of 0.85 and 0.95 have been accepted as criteria for a successful identification (Williams, S. T., et al., (1983), supra; Priest, F. G. and Austin, B., (1988), supra). The taxonomic distance of the unknown from the cluster centroid is calculated and may be compared to the radius of the cluster. The standard error of the taxonomic distance should be less than the upper value of +3.0 suggested by Sneath, P. H. A. ((1979), pp. 195–213). Moreover, physical characteristics, additional biochemical data and chemotaxomomic markers may be used to further confirm the identity of the unknown in a particular cluster.

Production and Application of Alkalitolerant Enzymes

The alkaliphilic microorganisms of the present invention produce a variety of enzymes. These enzymes are capable of performing their functions at an extremely high pH, making them uniquely suited for their application in a variety of processes requiring such enzymatic activity in high pH environments or reaction conditions.

Examples of the various applications for alkalitolerant enzymes are in detergent compositions, leather tanning, food treatment, waste treatment and in the textile industry. These enzymes may also be used for biotransformations, especially in the preparation of pure enantiomers.

The alkaliphiles may easily be screened for the production of alkalitolerant enzymes having lipolytic, proteolytic and/or starch-degrading activity using the methods described in Appendix B.

The broth in which alkaliphilic bacteria are cultured typically contains one or more types of enzymatic activity. The broth containing the enzyme or enzymes may be used directly in the desired process after the removal of the bacteria therefrom by means of centrifugation or filtration, for example.

If desired, the culture filtrate may be concentrated by freeze drying, before or after dialysis, or by ultrafiltration. The enzymes may also be recovered by precipitation and filtration. Alternatively, the enzyme or enzymes contained in the broth may be isolated and purified by chromatographic means or by gel electrophoresis, for example, before being applied to the desired process.

The genes encoding alkalitolerant enzymes of interest may be cloned and expressed in organisms capable of expressing the desired enzyme in a pure or easily recoverable form.

In one embodiment, the enzymatic preparation may be used in wash tests to determine the efficacy of the enzymatic activity.

Enzyme preparations from the alkaliphilic bacteria may be tested in a specially developed mini-wash test using cotton swatches soiled, for example, with protein-, lipid- and/or starch-containing components. Prior to the wash test, the swatches can be pre-treated with a solution containing an anionic surfactant, sodium perborate and a bleach activator (TAED). After this treatment, the test swatches are rinsed in running demineralized water and air-dried. This treatment results in the fixation of the soil, making its removal more difficult.

The washing tests may be performed using a defined detergent composition plus a specific amount of enzymatic activity in the presence of the test swatches. After washing, the swatches are rinsed in running demineralized water and air-dried. The reflectance of the test swatches is measured with a photometer.

The following example is provided to further illustrate the present invention and is not intended to limit the scope of the invention in any way.

EXAMPLE 1

Identification of an Unknown Isolate

Strain ML207a is a Gram-positive, alkaliphilic bacterium isolated from Mono Lake, a hypersaline, alkaline lake situated in California, U.S.A. (Javor, B., in *Hypersaline Environments*; Springer-Verlag, Berlin and Heidelberg, (1989), pp. 303–305) by plating out (on Medium A, Appendix A) mud and water samples collected in May, 1990. Strain ML207a is a coccus, forming bright yellow-orange, circular, entire, convex colonies on alkaline nutrient agar (Medium A).

Strain ML207a was examined using 22 of the minimum tests listed in Table 14. The character states were determined and identification scores obtained using the MATIDEN program. The results are outlined in Table 19. These indicate a very satisfactory identification of strain ML207a to Cluster 1, despite assigning only 22 of the 32 character states from the minimum discriminatory tests.

A Willcox probability of 0.9997 was calculated, which is significantly higher than the limit set at 0.95. Willcox probabilities of 0.85 and 0.95 have been accepted as criteria for a successful identification, (Williams, S. T., et al., (1983), supra; Priest, F. G. and Austin, B., (1988), supra). A taxonomic distance from the cluster centroid of 0.423 is acceptable and within the cluster radius defined at 0.539 (99% level). The standard error of the taxonomic distance at 2.076 is less than the upper value of +3.0 suggested by Sneath, P. H. A. ((1979), pp. 195–213). In addition, the coccus-shaped cells and yellow-orange colony color of strain ML207a also conform with the characteristics of Cluster 1 (Table 13).

TABLE 19

Example of the Output from the MATIDEN Program to Identify an Unknown Strain against the Identification Matrix Reference number of unknown is ML207a.

| Character | | Value in Unknown | Percent in: Best Taxon | Next Best Taxon |
|---|---|---|---|---|
| [10] | Gelatin | n.t. | 99 | 1 |
| [14] | Fumarate | − | 20 | 1 |
| [15] | Fructose | − | 60 | 1 |
| [19] | Galactose | + | 20 | 1 |
| [24] | N-acetylglucosamine | − | 1 | 25 |
| [27] | D-saccharose | − | 1 | 1 |
| [28] | Maltose | − | 20 | 25 |
| [32] | Acetate | − | 20 | 75 |
| [36] | D-glucose | − | 20 | 25 |
| [37] | Salicin | − | 1 | 25 |
| [38] | D-melibiose | − | 1 | 1 |
| [42] | Propionate | − | 1 | 75 |
| [44] | Valerate | − | 20 | 50 |
| [48] | Glycogen | − | 1 | 1 |
| [50] | L-serine | + | 40 | 1 |
| [63] | Chymotrypsin | + | 40 | 25 |
| [70] | β-glucosidase | − | 20 | 1 |
| [74] | Serine | + | 1 | 75 |
| [77] | Arginine | n.t. | 1 | 99 |
| [80] | Methionine | n.t. | 1 | 99 |
| [90] | Penicillin G | + | 99 | 50 |
| [94] | Methicillin | + | 99 | 99 |
| [96] | Streptomycin | + | 40 | 75 |
| [97] | Tetracyclin | − | 80 | 99 |
| [105] | Bacitracin | + | 99 | 99 |
| [112] | N-acetyl-D-glucosamine | n.t. | 40 | 1 |
| [116] | Cellobiose | n.t. | 1 | 1 |
| [137] | Turanose | n.t. | 40 | 1 |
| [139] | Methyl pyruvate | n.t. | 60 | 99 |
| [140] | Mono-methylsuccinate | n.t. | 40 | 99 |
| [192] | Thymidine | n.t. | 80 | 50 |
| [197] | Glycerol | n.t. | 80 | 25 |

Isolate ML207a best identification is Cluster 1
Scores for coefficients: 1 (Willcox probability), 2 (Taxonomic distance), 3 (Standard error of taxonomic distance).

| | 1 | 2 | 3 |
|---|---|---|---|
| CLUSTER 1 | 0.9997 | 0.423 | 2.076 |
| CLUSTER 2 | $0.261 \times 10^{-3}$ | 0.500 | 5.55 |
| CLUSTER 3 | $0.40 \times 10^{-3}$ | 0.540 | 6.60 |

| | | CLUSTER 1 | |
|---|---|---|---|
| CHARACTERS AGAINST | | % in Taxon | Value in unknown |
| [19] | Galactose | 20 | + |
| [74] | Serine | 1 | + |
| [97] | Tetracyclin | 80 | − |

ADDITIONAL CHARACTERS THAT ASSIST IN SEPARATING

| | | CLUSTER 1 from CLUSTER 4 | |
|---|---|---|---|
| | | % | % |
| [10] | Gelatin | 99 | 1 |
| [77] | Arginine | 1 | 99 |
| [80] | Methionine | 1 | 99 | n.t. = not tested.

EXAMPLE 2

Production of Proteolytic Enzymes

Five alkaliphilic strains (60E.4, 80LN.4, 81LN.4, wN10 and wN12) were tested for the production of proteolytic enzyme(s) in a medium poised at an alkaline pH. The experiments were carried out in 2 liter shake flasks provided with a baffle. Each of the flasks contained 400 ml of Medium S. Medium S had the following composition in g per liter: fresh yeast, 8.25; glucose, 1.32; $K_2HPO_4$; 1.6; $CaCl_2$, 0.05; $MgSO_4$, $7H_2O$, 0.05; $FeSO_4$, 0.005; $MnSO_4$, 0.0066; NaCl, 40.0. The medium was sterilized at 121° C. for 20 minutes and adjusted to pH 10.5 with sterile 40% $Na_2CO_3$ solution. The flasks were placed in an orbital incubator rotating at 280 revolutions per minute at a constant temperature of 37° C. Samples of culture medium were removed from the flasks at intervals of 0–5.7 days for the determination of enzyme content which is expressed in Alkaline Delft Units (ADU—as described in U.S. Pat. No. 4,002,572).

Table 20 shows the enzyme yield and the pH of the cultivation medium at the moment at which the measurement of enzyme levels were made.

water bath (2 cm stroke) and agitated at 200 revolutions per minute. The test were carried out at 40° C. for 30 minutes. After washing, the swatches were rinsed in running demineralized water for 10 minutes and air-dried. The reflectance on both sides of the test swatches was measured at 680 nm with a Photovolt photometer (Model 577) equipped with a green filter.

The wash performance of the supernatant fraction of cultures of several alkaliphilic bacteria in European powder detergents was determined according to the method specified above. The supernatant fractions were concentrated by ultrafiltration (Millipore CX Agitator or Amicon RA 2000 spiral ultrafiltrator) so as to produce an enzyme-containing preparation of at least 300 ADU/ml.

100 ml Erlenmeyer flasks were charged with powder detergent IEC dissolved in standard tap water of 15° German

TABLE 20

Production of Proteolytic Enzymes

| Day | Strain 60E.4 ADU/ml | pH | Strain 80LN.4 ADU/ml | pH | Strain 81LN.4 ADU/ml | pH | Strain wN10 ADU/ml | pH | Strain wN12 ADU/ml | pH |
|---|---|---|---|---|---|---|---|---|---|---|
| 0 | 0 | 10.5 | 0 | 10.5 | 0 | 10.5 | 0 | 10.5 | 0 | 10.5 |
| 1 | 137 | 9.5 | 2 | 10 | 16 | 10 | 0 | 10.5 | 2 | 10 |
| 2 |  |  | 2 | 9.5 | 18 | 10 | 0 | 10 |  |  |
| 3 | 122 | 10 | 3 | 10 | 17 | 10 | 2 | 10 |  |  |
| 4 | 101 | 10 |  |  |  |  |  |  |  |  |
| 5 | 88 | 10 | 3 | 10 | 15 | 10 | 5 | 10 | 5 | 10 |
| 7 | 74 | 10 |  |  | 14 | 10 |  |  |  |  |
| 9 | 58 | 10.5 | 5 | 10 | 14 | 10 | 5 | 10 | 3 | 10 |

The results of the test, together with the results shown in Appendix E clearly indicate the presence of proteolytic enzymes, produced by the alkaliphilic bacteria of the present invention, in the culture broth.

EXAMPLE 3

Wash Performance Test Using Proteolytic Enzymes

Enzyme preparations from the alkaliphilic bacteria were tested in a specially developed mini-wash test using swatches (2.5×2.5 cm) soiled with milk, blood and ink (obtained from EMPA, St. Gallen, Switzerland). Two types of fabric were tested; 100% cotton (designated EMPA 116) and polyester (35%)/cotton (65%) (designated EMPA 117). The test swatches were submitted to the mini-wash test either with or without a pretreatment ("pre-oxidized"). The pretreatment consisted of placing the swatches in a solution containing an anionic surfactant, sodium perborate and a bleach activator (TAED) and stirring at ambient temperature for 15 minutes. After this treatment the test swatches were rinsed in running demineralized water for 10 minutes and air-dried. This treatment results in the fixation of the remaining soil.

The washing tests were performed in 100 ml Erlenmeyer flasks provided with a baffle and containing 30 ml of a defined detergent composition plus 300 ADU (Alkaline Delft Units—as described in U.S. Pat. No. 4,002,572) protease to be tested. In each flask were placed two EMPA test swatches. The flasks were placed in a reciprocal shaking Hardness so as to give a final concentration of 4 g per liter, or IEC (3.2 g per liter) plus sodium perborate (0.74 g per liter) and TAED (0.6 g per liter) final concentrations in standard tap water.

The composition of the powder detergent IEC was as follows:

| Component | wt % |
|---|---|
| Linear sodium alkyl benzene sulphonate | 6.4 |
| Ethoxylated tallow alcohol | 2.3 |
| Sodium soap | 2.8 |
| Sodium tripolyphosphate | 35.0 |
| Sodium silicate | 6.0 |
| Magnesium silicate | 1.5 |
| Carboxymethylcellulose | 1.0 |
| Sodium sulphate | 16.8 |
| Miscellaneous + water | up to 100 |

Standard tap water is composed of $CaCl_2.2H_2O$, 0.291 g/l; $MgCl.6H_2O$, 0.140 g/l and $NaHCO_3$, 0.210 g/l dissolved in demineralized water.

To each flask, two EMPA test swatches were added and sufficient enzyme-containing preparations to give a final activity of 300 ADU. The final volume of the sud was 30 ml. By way of comparison, one flask contained no enzyme preparation, which was replaced with sterile bacterial culture medium. The results are shown in Tables 21 and 22.

TABLE 21

Application Washing Trials
Performance of Proteolytic Enzyme-Containing Preparation
from Alkaliphilic Bacterium 60E.4.
Average Remission of Test Swatches

| | IEC | | | IEC + PERBORATE + TAED | | |
|---|---|---|---|---|---|---|
| TEST SWATCH | CONTROL | ENZYME PREP. | % IMPROV-EMENT | CONTROL | ENZYME PREP. | % IMPROV-EMENT |
| EMPA 116 | 22.7 | 34.3 | 51.0 | | | |
| EMPA 116 (oxidized) | 12.5 | 12.9 | 3.2 | 12.0 | 12.7 | 5.8 |
| EMPA 117 | 20.2 | 48.1 | 138.2 | | | |
| EMPA 117 (oxidized) | 12.8 | 14.5 | 13.3 | 13.0 | 13.1 | 1.0 |

TABLE 22

Application Washing Trials
Performance of Proteolytic Enzyme-Containing Preparation
from Alkaliphilic Bacterium 81LN.4.
Average Remission of Test Swatches

| | IEC | | | IEC + PERBORATE + TAED | | |
|---|---|---|---|---|---|---|
| TEST SWATCH | CONTROL | ENZYME PREP. | % IMPROV-EMENT | CONTROL | ENZYME PREP. | % IMPROV-EMENT |
| EMPA 116 | 20.3 | 25.9 | 27.9 | | | |
| EMPA 116 (oxidized) | | | | 11.4 | 13.7 | 19.7 |
| EMPA 117 | 18.8 | 31.1 | 65.22 | | | |
| EMPA 117 (oxidized) | | | | 12.4 | 13.0 | 5.3 |

The results of the trials demonstrate the efficacy of the proteolytic enzymes produced by the strains of the present invention in a detergent formulation and the improved washing performance obtained.

EXAMPLE 4

Production of Starch Degrading Enzymes

Three alkaliphilic strains (60E.4, wN12 and wN16) were tested for the production of starch degrading enzymes on a starch containing medium poised at an alkaline pH.

The experiments were carried out in boiling tubes (2×20 cm) charged with 10 ml of alkaline medium Y. Medium Y had the following composition in g per liter demineralized water: yeast extract (Difco), 1.0; $KNO_3$, 10.0: $KH_2PO_4$, 1.0; $MgSO_4.7H_2O$, 0.2; $Na_2CO_3$, 10.0; NaCl, 40.0; soluble starch (Merck), 20.0. The tubes were inoculated (5%) with cells grown for 24 hours on medium A (see Appendix A) at 37° C. As controls, similar tubes of alkaline medium not containing starch were also inoculated.

The tubes were placed in an orbital shaking incubator rotating at 280 revolutions per minute, at a constant temperature of 37° C. for 72 hours. The fluid containing the enzyme activity was separated from the cells by centrifugation for 10 minutes at 4000 r.p.m.

The enzyme activity of the supernatant fraction was assayed by measuring the reducing sugars released as glucose from waxy maize starch and quantified with para-hydroxybenzoic acid hydrazide by using a method based on that of Lever, M. (1973), Biochem. Med. 7, 274–281. The reaction mixture (1.0 ml) contained 0.25% (w/v) waxy maize starch suspended in 0.1M sodium carbonate buffer, pH 10 (0.9 ml) and enzyme-containing supernatant (0.1 ml). The assays were carried out at 25° C. for 30 minutes and the reaction terminated by the addition of 3 ml para-hydroxybenzoic acid hydrazide reagent. After boiling for 5 minutes the absorbance at: 410 nm was measured in a spectrophotometer. The reducing sugars were measured as glucose equivalents from a standard curve.

One unit of starch degrading enzyme activity is defined as 1 $\mu$g of reducing sugars measured as glucose released per milliliter per minute at pH 10 and 25° C.

The number of starch degrading enzyme units formed is shown in Table 23.

TABLE 23

Production of Starch Degrading Enzymes

| MEDIUM Y | Strain 60E.4 | Strain wN12 | Strain wN16 |
|---|---|---|---|
| plus starch | 33,333 | 9,088 | 6,158 |
| no starch | 404 | 140 | 246 |

The results of the test, together with the results shown in Appendix E clearly indicate the presence of starch degrading enzymes, produced by the alkaliphilic bacteria of the present invention.

EXAMPLE 5

Stability of Starch Degrading Enzymes in Detergent

The ability of starch degrading enzymes from strains 60E4 and wN12 to withstand detergents, which is essential for their application in textile desizing, is demonstrated.

100 ml Erlenmeyer flasks provided with a baffle were each charged with 30 ml of 0.1M $Na_2CO_3NaHCO_3$ buffer, pH 10.1 containing 0.12 g of sodium dodecyl sulphate (equivalent to 4 g per liter). To one half of the flasks 0.3 g potato starch (equivalent to 1%) was added.

Each flask was dosed with enzyme-containing supernatant from the test strain by adding 0.5, 1.0 or 2.0 ml (see Table 24). As a control, the supernatant fluid was replaced with 1.0 ml water. Immediately after adding the enzyme, a 0.1 ml sample was removed (time=zero hours) for the measurement of enzyme activity using the para-hydroxybenzoic acid hydrazide method.

The flasks were incubated with shaking at 25° C. for 2.5 hours at which time a second 0.1 ml sample was removed for the measurement of enzyme activity.

As a comparison the experiment was repeated using a conventional α-amylase (Maxamyl$^R$) from *Bacillus amyloliquifaciens*.

Enzyme activity was determined using the reducing sugars method quantified by para-hydroxybenzoic acid hydrazide described previously.

The results are recorded in Table 24.

TABLE 24

Stability of Starch Degrading Enzymes in Detergent

| STRAIN | ENZYME-CONTAINING SUPERNATANT ADDED (ml) | CONDITIONS | ENZYME UNITS RECOVERED 0 hours | 2.5 hours |
|---|---|---|---|---|
| | 0* | SDS + STARCH | 0 | 0 |
| 60E4 | 0.5 | SDS + | <1 | 32 |
| | 1.0 | STARCH | 13 | 77 |
| | 2.0 | | 36 | 132 |
| 66B4 | 0.5 | SDS + | 3 | 33 |
| | 1.0 | STARCH | 6 | 65 |
| | 2.0 | | 13 | 119 |
| | Standard §) | SDS | 27 | 27 |
| | Standard §) | SDS + STARCH | 29 | 48 |

*replaced with 1 ml water

§)250 TAU Maxamyl$^R$ amylase (one TAU, Thermophile Amylase Unit, is defined as the quantity of enzyme that will convert 1 mg starch per minute at pH 6.6 and 30° C. into a product which upon reaction with iodine has an equal absorbance at 620 nm as a solution containing 25 g $CoCl_2.6$ $H_2O$, 3.84 g $K_2Cr_2O_7$ and 1 ml HCl in 100 ml distilled water.

The results of this test clearly demonstrate the stability of starch degrading enzymes, produced by the alkaliphilic enzyme of the present invention, in the presence of detergent.

Appendix A

Media Used in the Present Invention

MEDIUM A

| | | |
|---|---:|---|
| Glucose | 10.0 | $gl^{-1}$ |
| Peptone (Difco: Detroit, MI, USA) | 5.0 | $gl^{-1}$ |
| Yeast Extract (Difco) | 5.0 | $gl^{-1}$ |
| $K_2HPO_4$ | 1.0 | $gl^{-1}$ |
| $MgSO_4 \cdot 7H_2O$ | 0.2 | $gl^{-1}$ |
| NaCl | 40.0 | $gl^{-1}$ |
| $Na_2CO_3$ | 10.0 | $gl^{-1}$ |
| * Agar | 20.0 | $gl^{-1}$ |

\* (when required for a solid medium)

MEDIUM B

| | | |
|---|---:|---|
| Glucose | 10.0 | $gl^{-1}$ |
| Peptone (Difco) | 5.0 | $gl^{-1}$ |
| Yeast Extract (Difco) | 5.0 | $gl^{-1}$ |
| $K_2HPO_4$ | 1.0 | $gl^{-1}$ |
| $MgSO_4 \cdot 7H_2O$ | 0.2 | $gl^{-1}$ |
| NaCl | 40.0 | $gl^{-1}$ |
| $Na_2CO_3$ | 10.0 | $gl^{-1}$ |
| Lactalbumin | 10.0 | $gl^{-1}$ |
| Agar | 20.0 | $gl^{-1}$ |

MEDIUM C

| | | |
|---|---:|---|
| Glucose | 10.0 | $gl^{-1}$ |
| Peptone (Difco) | 5.0 | $gl^{-1}$ |
| Yeast Extract (Difco) | 5.0 | $gl^{-1}$ |
| $K_2HPO_4$ | 1.0 | $gl^{-1}$ |
| $MgSO_4 \cdot 7H_2O$ | 0.2 | $gl^{-1}$ |
| NaCl | 40.0 | $gl^{-1}$ |
| $Na_2CO_3$ | 10.0 | $gl^{-1}$ |
| Casein | 20.0 | $gl^{-1}$ |
| Agar | 20.0 | $gl^{-1}$ |

MEDIUM D

| | | |
|---|---:|---|
| Soluble Starch | 10.0 | $gl^{-1}$ |
| Peptone (Difco) | 5.0 | $gl^{-1}$ |
| Yeast Extract (Difco) | 5.0 | $gl^{-1}$ |
| $K_2HPO_4$ | 1.0 | $gl^{-1}$ |
| $MgSO_4 \cdot 7H_2O$ | 0.2 | $gl^{-1}$ |
| NaCl | 40.0 | $gl^{-1}$ |
| $Na_2CO_3$ | 10.0 | $gl^{-1}$ |
| Lactalbumin | 10.0 | $gl^{-1}$ |
| Agar | 20.0 | $gl^{-1}$ |

Appendix A (continued)

MEDIUM E

| | | |
|---|---|---|
| Soluble Starch | 10.0 | gl$^{-1}$ |
| Peptone (Difco) | 5.0 | gl$^{-1}$ |
| Yeast Extract (Difco) | 5.0 | gl$^{-1}$ |
| K$_2$HPO$_4$ | 1.0 | gl$^{-1}$ |
| MgSO$_4 \cdot$7H$_2$O | 0.2 | gl$^{-1}$ |
| NaCl | 40.0 | gl$^{-1}$ |
| Na$_2$CO$_3$ | 10.0 | gl$^{-1}$ |
| Casein | 20.0 | gl$^{-1}$ |
| Agar | 20.0 | gl$^{-1}$ |

MEDIUM F

| | | |
|---|---|---|
| Oxbile (Oxoid: Basingstoke, U.K.) | 10.0 | gl$^{-1}$ |
| (NH$_4$)$_2$SO$_4$ | 5.0 | gl$^{-1}$ |
| MgSO$_4 \cdot$7H$_2$O | 0.2 | gl$^{-1}$ |
| Yeast Extract (Difco) | 0.5 | gl$^{-1}$ |
| Lactalbumin | 10.0 | gl$^{-1}$ |
| Agar | 20.0 | gl$^{-1}$ |

Adjusted to pH 8.5 with 50% Na$_2$CO$_3$ solution

MEDIUM G

| | | |
|---|---|---|
| Oxbile (Oxoid) | 10.0 | gl$^{-1}$ |
| (NH$_4$)$_2$SO$_4$ | 5.0 | gl$^{-1}$ |
| MgSO$_4 \cdot$7H$_2$O | 0.2 | gl$^{-1}$ |
| Yeast Extract (Difco) | 0.5 | gl$^{-1}$ |
| Casein | 20.0 | gl$^{-1}$ |
| Agar | 20.0 | gl$^{-1}$ |

Adjusted to pH 8.5 with 50% Na$_2$CO$_3$ solution

66

Appendix B

Methods for Unit Tests

1. Character numbers 1 to 5
   Colony color, form, elevation, margin, size
   A suspension of bacteria was spread over an alkaline nutrient agar (Medium A) and cultivated at 37°C. Colonies were examined after 48 hours.

2. Character numbers 6 and 7
   Cell morphology, Gram's strain reaction
   Bacteria cells grown in alkaline nutrient broth (Medium A, without agar) for 24 hours were spun down in a centrifuge and resuspended in a small amount of alkaline nutrient broth and allowed to air-dry on a microscope slide. Or, bacteria were cultivated for 24 -48 hours on an alkaline nutrient agar (Medium A) so as to form colonies. Colonies of bacteria were suspended in physiological saline and a few drops allowed to air-dry on a microscope slide. The Grams's straining test was performed using the Dussault modification (Dussault, H.P. (1955) Journal of Bacteriology, 70, pp. 484-485) with safranin as counterstain.

3. Character number 8
   Oxidase reaction
   Filter paper moistened with a 1% aqueous solution of N,N,N',N'-tetramethyl-p-phenylenediamine or oxidase identification discs (bioMérieux: Charbonières-les-Bains, France) were smeared with a young bacterial culture from alkaline nutrient agar. A purple color within 1 minute was recorded as a positive reaction. *E. coli*, used as a control, did not give a positive reaction within one minute.

4. Character number 9
   Aminopeptidase reaction
   The test was performed using the diagnostic test strips Bactident$^R$ Aminopeptidase (E. Merck; Darmstadt, Germany). A yellow color within 30 minutes was recorded as a positive reaction.

5. Character number 10
   Gelatin hydrolysis
   Charcoal-gelatin discs (bioMérieux) or "chargels" (Oxoid) were incubated at 37°C in an alkaline nutrient broth (Medium A) together with bacteria. A black sediment indicated a positive reaction.

Appendix B (continued)

6. Character number 11
   Skim milk test
   A minimal medium composed (g/l distilled water) of yeast extract, 1.0; $KNO_3$, 10.0; $K_2HPO_4$, 1.0; $MgSO_4 \cdot 7H_2O$, 0.2; NaCl, 40.0; $Na_2CO_3$, 10.0; agar, 20.0 was supplemented with 5.0 g/l skim milk powder, sterilised by autoclaving and poured into Petri dishes. Bacteria were inoculated and incubated at 37°C. Areas of clearing around bacterial colonies in an otherwise opaque agar were recorded as a positive reaction.
   Non-alkaliphilic reference strains were tested in an identical fashion using media of the same composition but without $Na_2CO_3$ so as to give a pH of 6.8-7.0.

7. Character number 12
   NaCl tolerance
   Two methods were applied.
   (a) Bacterial strains were cultivated at 37°C on an alkaline nutrient agar (Medium A) containing 0%, 4%, 8%, 12% or 15% (w/v) NaCl. The agar plates were examined for bacterial growth after 48 hours.
   (b) Bacterial strains were cultivated at 37°C in an alkaline nutrient broth (Medium A) containing 0%, 4%, 8%, 12%, 15% or 25% NaCl. Bacterial growth was monitored by optical density measurements using a Klett meter (green filter) at 0, 12, 24, 48, 72 and 144 hours.

8. Character number 13
   Minimum pH for growth
   Nutrient agar, pH 6.8-7.0 (Medium A without sodium carbonate) was poured into square Petri dishes. A strip of solidified agar was removed from one end and replaced with molten 4% (w/v) agar containing 3.6% (w/v) $Na_2CO_3$ and 0.8% (w/v) NaOH. A pH gradient from pH 10.5 to pH 7 across the plate was allowed to develop overnight. Bacteria were incoculated by streaking along the pH gradient and cultivated at 37°C for 48 hours. The pH at the point where bacterial growth ceased was measured with a flat head electrode and with "Alkalite" pH strips (Merck: Darmstadt, W. Germany).

Appendix B (continued)

9. Character numbers 14 - 22
   Carbohydrate utilisation
   A minimal medium composed (g/l distilled water) of yeast extract, 1.0; $KNO_3$, 10.0; $K_2HPO_4$, 1.0; $MgSO_4 \cdot 7H_2O$, 0.2; NaCl, 40.0; $Na_2CO_3$, 10.0; agar, 20.0 was supplemented with 2.0 g/l of the carbohydrate under test and poured into square Petri dishes. Bacteria were inoculated, using a 25 point multi-point inoculator, from 1.0 ml of a bacterial suspension cultivated for 48 hours in an alkaline nutrient broth (Medium A). The agar-plates were incubated at 37°C for 48 hours. The results were recording by comparing bacterial growth on minimal nutrient medium containing a carbohydrate supplement with growth on a minimal medium without the carbohydrate under test.
   Non-alkaliphilic reference strains were tested in an identical fashion using media of the same composition but without $Na_2CO_3$ so as to give a pH of 6.8-7.0.

10. Character numbers 23 - 54
    Growth on carbon substrates
    Use was made of the commercially available test strip ATB 32 GN (API-bioMérieux: La Balme les Grottes, France). The strips were used according to the manufacturer's instructions but with an addition of 1.0 ml of a solution containing 4% NaCl and 1% $Na_2CO_3$ to the vials of basal medium provided. The strips were incubated at 37°C for 48 hours.
    Non-alkaliphilic reference strains were incubated in the standard basal medium.

11. Character numbers 55 - 73
    Enzymatic activities
    Use was made of the commercially available test strip APIZYM (API-bioMérieux) which was used according to the manufacturer's instructions, except that the alkaliphilic bacterial cells were suspended in alkaline nutrient broth (Medium A). The strips were incubated at 37°C for 24 hours.

12. Character numbers 74 - 83
    Amino acids as carbon and nitrogen source
    The same technique was employed as for tests 14 - 21 except that $KNO_3$ was omitted from the minimal nutrient medium.

- 69 -

Appendix B (continued)

13. Character numbers 84 - 105
    Antibiotic sensitivity
    A light suspension of bacteria in alkaline nutrient broth was spread on the surface of alkaline nutrient agar (Medium A) and allowed to dry. Commercially available antibiotic susceptibility test discs (Oxoid or Mast Laboratories: Merseydide, U.K.) were applied to the agar surface. The bacteria were cultivated at 37°C for 48 hours. Clear zones around the antibiotic discs indicated sensitivity.

14. Character numbers 106 - 200
    Biolog GN system
    Use was made of the commercially available bacterial identification system, GN MicroPlates™ (Biolog, Inc., Hayward, California, U.S.A.) which permits the performance of 95 carbon source utilization reactions. The plates were used according to the manufacturer's instructions except that alkaliphilic bacterial cells were suspended in a fluid composed of (g/l); NaCl, 40.0; $KNO_3$, 1.0; which was adjusted to pH 8.5-9 with a 40% w/v solution of $Na_2CO_3$, and sterilised by filtration. The bacterial cell suspensions were adjusted to an optical density of 80 - 100 units on a model 900-3 Klett-Summerson photoelectric colorimeter (green filter) (approximately equivalent to 2 on the MacFarland scale). The plates were inoculated and incubated at 37°C in a moist chamber. The plates were read at 6 hours and 24 hours, and the results recorded by visual inspection and on a microplate reader (Anthos model 2001 at 620 nm or a Dynatech model MR600 at 570 nm).

Note: in the above tests, *Exiguobacterium aurantiacum* was cultivated at 25°C; *Brevibacterium linens* and *Micrococcus luteus* were cultivated at 30°C, all other strains were cultured at 37°C.

- 78 -

Appendix C

Unit Tests for Analysis by Numerical Taxonomy

| CHARACTER NUMBER | TEST DESCRIPTION | COMPUTER CODING Multistate | Two-state |
|---|---|---|---|
| 1. | Colony color | white = 1<br>cream = 2<br>beige = 3<br>yellow = 4<br>orange = 5<br>pink = 6<br>brown = 7<br>red = 8 | not used |
| 2. | Colony form | circular = 1<br>irregular = 2<br>punctiform = 3 | not used |
| 3. | Colony elevation | convex = 1<br>raised = 2<br>umbonate = 3<br>flat = 4 | not used |
| 4. | Colony margin | entire = 1<br>undulate = 2<br>lobate = 3<br>fimbriate = 4 | not used |
| 5. | Colony size | diameter in millimeters | not used |
| 6. | Cell morphology | rod = 1<br>coccobacillus = 1<br>coccus = 2 | = 0<br>= 0<br>= 1 |
| 7. | Gram's stain | negative = 1<br>positive = 2 | = 0<br>= 1 |
| 8. | Oxidase reaction | negative = 1<br>positive = 2 | = 0<br>= 1 |
| 9. | Aminopeptidase reaction | negative = 1<br>positive = 2 | = 0<br>= 1 |
| 10. | Gelatin hydrolysis | negative = 1<br>positive = 2 | = 0<br>= 1 |
| 11. | Skim milk test | negative = 1<br>positive = 2 | = 0<br>= 1 |

Appendix C (continued)

| CHARACTER NUMBER | TEST DESCRIPTION | COMPUTER CODING | | |
|---|---|---|---|---|
| | | Multistate | | Two-state |
| 12. | NaCl tolerance | growth at 0-4% | = 1 | not used |
| | | growth at 0-8% | = 2 | |
| | | growth at 0-12% | = 3 | |
| | | growth at 0-15% | = 4 | |
| | | growth only at 0% | = 5 | |
| | | growth only at 4-15% | = 6 | |
| 13. | Minimum pH for growth on nutrient agar | pH 7.0 | = 7 | not used |
| | | pH 7.5 | = 7.5 | |
| | | pH 8.0 | = 8 | |
| | | pH 8.5 | = 8.5 | |
| | | pH 9.0 | = 9 | |
| | | pH 9.5 | = 9.5 | |
| | | pH 10.0 | = 10 | |
| | | pH 10.5 | = 10.5 | |
| 14-22 | Carbohydrate utilization | | | |
| 14. | Fumarate | | | |
| 15. | Fructose | | | |
| 16. | Succinate | | | |
| 17. | Formate | enhanced growth | = 2 | = 1 |
| 18. | Lactose | equal growth | = 1 | = 0 |
| 19. | Galactose | growth inhibited | = 0 | = 0 |
| 20. | Xylose | | | |
| 21. | Pyruvate | | | |
| 22. | Starch | | | |
| 23-54 | Growth on carbon substrates | | | |
| 23. | Rhamnose | | | |
| 24. | N-acetylglucosamine | | | |
| 25. | D-ribose | | | |
| 26. | Inositol | positive | = 2 | = 1 |
| 27. | D-saccharose | negative | = 1 | = 0 |
| 28. | Maltose | | | |
| 29. | Itaconate | | | |
| 30. | Suberate | | | |
| 31. | Malonate | | | |
| 32. | Acetate | | | |
| 33. | DL-lactate | | | |
| 34. | L-alanine | | | |
| 35. | Mannitol | | | |
| 36. | D-glucose | | | |
| 37. | Salicin | | | |
| 38. | D-melibiose | | | |
| 39. | L-fucose | | | |
| 40. | D-sorbitol | | | |
| 41. | L-arabinose | | | |
| 42. | Propionate | | | |

Appendix C (continued)

| CHARACTER NUMBER | TEST DESCRIPTION | COMPUTER CODING | |
|---|---|---|---|
| | | Multistate | Two-state |
| 43. | Caprate | | |
| 44. | Valerate | | |
| 45. | Citrate | | |
| 46. | Histidine | | |
| 47. | 5-ketogluconate | | |
| 48. | Glycogen | | |
| 49. | 3-hydroxybenzonate | | |
| 50. | L-serine | | |
| 51. | 2-ketogluconate | | |
| 52. | 3-hydroxybutyrate | | |
| 53. | 4-hydroxybenzoate | | |
| 54. | L-proline | | |
| 55-73 | Enzymatic activity | | |
| 55. | Alkaline phosphatase | | |
| 56. | Esterase (C4) | | |
| 57. | Esterase lipase (C8) | | |
| 58. | Lipase (C14) | | |
| 59. | Leucine arylamidase | | |
| 60. | Valine arylamidase | | |
| 61. | Cystine arylamidase | positive = 2 | = 1 |
| 62. | Trypsin | negative = 1 | = 0 |
| 63. | Chymotrypsin | | |
| 64. | Acid phosphatase | | |
| 65. | Naphthol-AS-BI-phosphohydrolase | | |
| 66. | α-galactosidase | | |
| 67. | β-galactosidase | | |
| 68. | β-glucuronidase | | |
| 69. | α-glucosidase | | |
| 70. | β-glucosidase | | |
| 71. | N-acetyl-β-glucosaminidase | | |
| 72. | α-mannosidase | | |
| 73. | α-fucosidase | | |
| 74-83 | Amino acids as carbon and nitrogen source | | |
| 74. | Serine | | |
| 75. | Proline | | |
| 76. | Asparagine | | |
| 77. | Arginine | enhanced growth = 2 | = 1 |
| 78. | Alanine | equal growth = 1 | = 0 |
| 79. | Lysine | no growth = 0 | = 0 |

Appendix C (continued)

| CHARACTER NUMBER | TEST DESCRIPTION | COMPUTER CODING | |
|---|---|---|---|
| | | Multistate | Two-state |
| 80. | Methionine | | |
| 81. | Phenylalanine | | |
| 82. | Glycine | | |
| 83. | Valine | | |
| 84-105 | Antibiotic sensitivity | | |
| 84. | Gentamycin 10 μg | | |
| 85. | Nitrofurantoin 50 μg | | |
| 86. | Ampicillin 25 μg | | |
| 87. | Nalidixic acid 30 μg | | |
| 88. | Sulphamethoxazole 50 μg | | |
| 89. | Trimethoprim 2.5 μg | | |
| 90. | Penicillin G 1 IU | | |
| 91. | Chloramphenicol 25 μg | | |
| 92. | Erythromycin 5 μg | antibiotic sensitive | |
| 93. | Fusidic acid 10 μg | inhibition of | |
| 94. | Methicillin 10 μg | growth = 2 | = 1 |
| 95. | Novobiocin 5 μg | | |
| 96. | Streptomycin 10 μg | antibiotic sensitive | |
| 97. | Tetracyclin 25 μg | no growth | |
| 98. | Sulphafurazole 100 μg | inhibition = 1 | = 0 |
| 99. | Oleandomycin 5 μg | | |
| 100. | Polymyxin 300 IU | | |
| 101. | Rifampicin 2 μg | | |
| 102. | Neomycin 30 μg | | |
| 103. | Vancomycin 30 μg | | |
| 104. | Kanmycin 30 μg | | |
| 105. | Bacitracin 10 IU | | |
| 106-200. | Biolog GN system | | |
| 106. | α-cyclodextrin | | |
| 107. | Dextrin | | |
| 108. | Glycogen | | |
| 109. | Tween 40 | | |
| 110. | Tween 80 | | |
| 111. | N-acetyl-D-galactosamine | | |
| 112. | N-acetyl-D-glucosamine | | |
| 113. | Adonitol | | |
| 114. | L-arabinose | | |
| 115. | D-arabitol | | |
| 116. | Cellobiose | | |
| 117. | i-erythritol | | |
| 118. | D-fructose | | |
| 119. | L-fucose | | |
| 120. | D-galactose | | |
| 121. | Gentiobiose | negative = 1 | = 0 |
| 122. | α-D-glucose | positve = 2 | = 1 |
| 123. | m-inositol | weak positive = 3 | = 1 |
| 124. | α-lactose | | |

Appendix C (continued)

| CHARACTER NUMBER | TEST DESCRIPTION | COMPUTER CODING Multistate | Two-state |
|---|---|---|---|
| 125. | Lactulose | | |
| 126. | Maltose | | |
| 127. | D-mannitol | | |
| 128. | D-mannose | | |
| 129. | D-melibiose | | |
| 130. | ß-methylglucoside | | |
| 131. | Psicose | | |
| 132. | D-raffinose | | |
| 133. | L-rhamnose | | |
| 134. | D-sorbitol | | |
| 135. | Sucrose | | |
| 136. | D-trehalose | | |
| 137. | Turanose | | |
| 138. | Xylitol | | |
| 139. | Methyl pyruvate | | |
| 140. | Mono-methylsuccinate | | |
| 141. | Acetic acid | | |
| 142. | Cis-aconitic acid | | |
| 143. | Citric acid | | |
| 144. | Formic acid | | |
| 145. | D-galactonic acid lactone | | |
| 146. | D-galacturonic acid | | |
| 147. | D-gluconic acid | | |
| 148. | D-glucosaminic acid | | |
| 149. | D-glucuronic acid | | |
| 150. | α-hydroxybutyric acid | | |
| 151. | ß-hydroxybutyric acid | | |
| 152. | gamma-hydroxybutyric acid | | |
| 153. | p-hydroxyphenylacetic acid | | |
| 154. | Itaconic acid | | |
| 155. | α-ketobutyric acid | | |
| 156. | α-ketoglutaric acid | | |
| 157. | α-ketovaleric acid | | |
| 158. | DL-lactic acid | | |
| 159. | Malonic acid | | |
| 160. | Propionic acid | | |
| 161. | Quinic acid | | |
| 162. | D-saccharic acid | | |
| 163. | Sebacic acid | | |
| 164. | Succinic acid | | |
| 165. | Bromo-succinic acid | | |
| 166. | Succinamic acid | | |
| 167. | Glucuronamide | | |
| 168. | Alaninamide | | |
| 169. | D-alanine | | |
| 170. | L-alanine | | |
| 171. | L-alanylglycine | | |
| 172. | L-asparagine | | |
| 173. | L-aspartic acid | | |
| 174. | L-glutamic acid | | |

Appendix C (continued)

| CHARACTER NUMBER | TEST DESCRIPTION | COMPUTER CODING | |
|---|---|---|---|
| | | Multistate | Two-state |
| 175. | Glycyl-L-aspartic acid | | |
| 176. | Glycyl-L-glutamic acid | | |
| 177. | L-histidine | | |
| 178. | Hydroxy L-proline | | |
| 179. | L-leucine | | |
| 180. | L-ornithine | | |
| 181. | L-phenylalanine | | |
| 182. | L-proline | | |
| 183. | L-pyroglutamic acid | | |
| 184. | D-serine | | |
| 185. | L-serine | | |
| 186. | L-threonine | | |
| 187. | DL-carnitine | | |
| 188. | gamma-aminobutyric acid | | |
| 189. | Urocanic acid | | |
| 190. | Inosine | | |
| 191. | Uridine | | |
| 192. | Thymidine | | |
| 193. | Phenylethylamine | | |
| 194. | Putrescine | | |
| 195. | 2-aminoethanol | | |
| 196. | 2,3-butanediol | | |
| 197. | Glycerol | | |
| 198. | DL-α-glycerol phosphate | | |
| 199. | Glucose-1-phosphate | | |
| 200. | Glucose-6-phosphate | | |

Appendix D

Percentage Positive States for Characters in Clusters

| | CHARACTER | CLUSTER | | | | | |
|---|---|---|---|---|---|---|---|
| | | 1 | 2 | 3 | 4 | 5 | 6 |
| [6] | Cell morphology | 60 | 0 | 0 | 0 | 0 | 0 |
| [7] | Gram's stain | 100 | 100 | 100 | 100 | 100 | 100 |
| [8] | Oxidase reaction | 20 | 60 | 0 | 25 | 83 | 75 |
| [9] | Aminopeptidase | 40 | 0 | 0 | 25 | 0 | 0 |
| [10] | Gelatin | 100 | 100 | 100 | 0 | 100 | 100 |
| [11] | Skim milk | 20 | 60 | 50 | 0 | 40 | 25 |
| [14] | Fumarate | 20 | 20 | 75 | 0 | 83 | 50 |
| [15] | Fructose | 60 | 80 | 75 | 0 | 83 | 100 |
| [16] | Succinate | 60 | 20 | 100 | 50 | 50 | 75 |
| [17] | Formate | 0 | 0 | 25 | 0 | 0 | 25 |
| [18] | Lactose | 0 | 20 | 0 | 0 | 17 | 0 |
| [19] | Galactose | 20 | 20 | 100 | 0 | 17 | 0 |
| [20] | Xylose | 0 | 40 | 0 | 0 | 17 | 25 |
| [21] | Pyruvate | 40 | 40 | 75 | 0 | 50 | 50 |
| [22] | Starch | 80 | 100 | 75 | 75 | 100 | 100 |
| [23] | Rhamnose | 20 | 20 | 0 | 0 | 17 | 75 |
| [24] | N-acetylglucosamine | 0 | 20 | 50 | 25 | 100 | 100 |
| [25] | D-ribose | 0 | 20 | 25 | 0 | 67 | 75 |
| [26] | Inositol | 20 | 40 | 25 | 0 | 33 | 75 |
| [27] | D-saccharose | 0 | 80 | 25 | 0 | 100 | 100 |
| [28] | Maltose | 20 | 100 | 0 | 25 | 100 | 100 |
| [29] | Itaconate | 0 | 20 | 0 | 0 | 0 | 0 |
| [30] | Suberate | 40 | 20 | 0 | 0 | 50 | 50 |
| [31] | Malonate | 60 | 20 | 0 | 25 | 67 | 25 |
| [32] | Acetate | 20 | 40 | 0 | 75 | 100 | 100 |
| [33] | DL-lactate | 60 | 40 | 25 | 25 | 83 | 100 |
| [34] | L-alanine | 20 | 20 | 0 | 25 | 83 | 50 |
| [35] | Mannitol | 20 | 60 | 25 | 0 | 83 | 100 |
| [36] | D-glucose | 20 | 80 | 0 | 25 | 100 | 100 |
| [37] | Salicin | 0 | 100 | 50 | 25 | 67 | 100 |
| [38] | D-melibiose | 0 | 40 | 0 | 0 | 50 | 100 |
| [39] | L-fucose | 0 | 20 | 0 | 0 | 0 | 25 |
| [40] | D-sorbitol | 20 | 20 | 25 | 0 | 17 | 75 |
| [41] | L-arabinose | 0 | 20 | 0 | 0 | 50 | 75 |
| [42] | Propionate | 0 | 0 | 0 | 75 | 83 | 100 |
| [43] | Caprate | 0 | 0 | 0 | 0 | 50 | 50 |
| [44] | Valerate | 20 | 0 | 0 | 50 | 83 | 50 |
| [45] | Citrate | 20 | 20 | 0 | 25 | 83 | 100 |
| [46] | Histidine | 0 | 0 | 0 | 25 | 50 | 0 |
| [47] | 5-ketogluconate | 0 | 0 | 0 | 0 | 17 | 50 |
| [48] | Glycogen | 0 | 80 | 0 | 0 | 100 | 100 |
| [49] | 3-hydroxybenzoate | 20 | 0 | 0 | 0 | 0 | 0 |
| [50] | L-serine | 40 | 0 | 25 | 0 | 17 | 100 |
| [51] | 2-ketogluconate | 20 | 20 | 0 | 0 | 67 | 75 |
| [52] | 3-hydroxybutyrate | 0 | 40 | 0 | 50 | 67 | 75 |

- 33 -

|  | CHARACTER | CLUSTER | | | | | |
|---|---|---|---|---|---|---|---|
|  |  | 1 | 2 | 3 | 4 | 5 | 6 |
| [53] | 4-hydroxybenzoate | 20 | 20 | 0 | 0 | 0 | 0 |
| [54] | L-proline | 40 | 40 | 0 | 25 | 83 | 100 |
| [55] | Alkaline phosphatase | 80 | 100 | 100 | 100 | 83 | 100 |
| [56] | Esterase (C4) | 100 | 100 | 100 | 100 | 100 | 100 |
| [57] | Esterase lipase(C8) | 100 | 100 | 100 | 100 | 100 | 100 |
| [58] | Lipase (C14) | 0 | 20 | 0 | 50 | 0 | 0 |
| [59] | Leucine arylamidase | 40 | 80 | 100 | 100 | 33 | 100 |
| [60] | Valine arylamidase | 20 | 20 | 50 | 75 | 0 | 0 |
| [61] | Cystine arylamidase | 0 | 0 | 25 | 50 | 17 | 0 |
| [62] | Trypsin | 20 | 0 | 50 | 25 | 0 | 75 |
| [63] | Chymotrypsin | 40 | 20 | 75 | 25 | 100 | 0 |
| [64] | Acid phosphatase | 100 | 60 | 100 | 100 | 100 | 100 |
| [65] | Naphthol phosphohydrolase | 20 | 60 | 50 | 50 | 50 | 100 |
| [66] | α-galactosidase | 20 | 60 | 25 | 0 | 17 | 100 |
| [67] | ß-galactosidase | 40 | 20 | 25 | 0 | 50 | 100 |
| [68] | ß-glucuronidase | 20 | 20 | 0 | 0 | 17 | 100 |
| [69] | α-glucosidase | 100 | 80 | 75 | 100 | 83 | 100 |
| [70] | ß-glucosidase | 20 | 100 | 100 | 0 | 33 | 100 |
| [71] | N-acetyl glucosaminidase | 20 | 20 | 0 | 0 | 0 | 75 |
| [72] | α-mannosidase | 0 | 40 | 25 | 0 | 0 | 75 |
| [73] | α-fucosidase | 0 | 0 | 0 | 0 | 0 | 0 |
| [74] | Serine | 0 | 100 | 0 | 75 | 50 | 0 |
| [75] | Proline | 80 | 80 | 100 | 100 | 83 | 0 |
| [76] | Asparagine | 60 | 40 | 100 | 100 | 50 | 0 |
| [77] | Arginine | 0 | 40 | 100 | 100 | 33 | 0 |
| [78] | Alanine | 40 | 40 | 25 | 75 | 33 | 50 |
| [79] | Lysine | 20 | 60 | 50 | 75 | 50 | 25 |
| [80] | Methionine | 0 | 100 | nc | 100 | 33 | 25 |
| [81] | Phenylalanine | 80 | 60 | 100 | 100 | 50 | 25 |
| [82] | Glycine | 20 | 60 | 0 | 100 | 33 | 0 |
| [83] | Valine | 0 | 60 | 25 | 100 | 17 | 0 |
| [84] | Gentamycin | 60 | 0 | 50 | 50 | 50 | 25 |
| [85] | Nitrofurantoin | 50 | 20 | 0 | 50 | 0 | 0 |
| [86] | Ampicillin | 80 | 100 | 0 | 100 | 100 | 25 |
| [87] | Nalidixic acid | 0 | 20 | 0 | 0 | 0 | 0 |
| [88] | Sulphamethoxazole | 0 | 0 | 0 | 0 | 0 | 0 |
| [89] | Trimethoprim | 25 | 0 | 25 | 50 | 83 | 50 |
| [90] | Penicillin G | 100 | 60 | 0 | 50 | 83 | 0 |
| [91] | Chloramphenicol | 80 | 80 | 100 | 100 | 100 | 75 |
| [92] | Erythromycin | 100 | 100 | 100 | 100 | 100 | 25 |
| [93] | Fusidic acid | 100 | 100 | 50 | 100 | 100 | 75 |
| [94] | Methicillin | 100 | 100 | 0 | 100 | 100 | 25 |
| [95] | Novobiocin | 0 | 25 | 0 | 0 | 0 | 25 |
| [96] | Streptomycin | 40 | 80 | 50 | 75 | 67 | 0 |
| [97] | Tetracyclin | 80 | 60 | 0 | 100 | 100 | 25 |
| [98] | Sulphafurazole | 25 | 25 | nc | 100 | 33 | 25 |
| [99] | Oleandomycin | 100 | 100 | 100 | 100 | 83 | 0 |
| [100] | Polymixin | 40 | 20 | 0 | 0 | 0 | 0 |

|  | CHARACTER | CLUSTER | | | | | |
|---|---|---|---|---|---|---|---|
|  |  | 1 | 2 | 3 | 4 | 5 | 6 |
| [101] | Rifampicin | 100 | 100 | 100 | 100 | 100 | 100 |
| [102] | Neomycin | 0 | 0 | 0 | 50 | 17 | 0 |
| [103] | Vancomycin | 100 | 80 | 100 | 100 | 100 | 50 |
| [104] | Kanamycin | 0 | 0 | 0 | 0 | 17 | 0 |
| [105] | Bacitracin | 100 | 100 | 100 | 100 | 83 | 0 |
| [106] | α-cyclodextrin | 0 | 20 | 25 | 100 | 17 | 25 |
| [107] | Dextrin | 100 | 60 | 75 | 75 | 100 | 75 |
| [108] | Glycogen | 60 | 60 | 50 | 75 | 83 | 75 |
| [109] | Tween 40 | 0 | 0 | 0 | 100 | 0 | 0 |
| [110] | Tween 80 | 0 | 0 | 0 | 75 | 0 | 0 |
| [111] | N-acetyl galactosamine | 0 | 0 | 0 | 0 | 0 | 0 |
| [112] | N-acetylglucosamine | 40 | 40 | 100 | 0 | 50 | 50 |
| [113] | Adonitol | 0 | 20 | 50 | 0 | 0 | 0 |
| [114] | L-arabinose | 0 | 20 | 50 | 0 | 17 | 0 |
| [115] | D-arabitol | 0 | 0 | 0 | 0 | 0 | 0 |
| [116] | Cellobiose | 0 | 40 | 100 | 0 | 50 | 0 |
| [117] | i-erythritol | 0 | 0 | 25 | 50 | 0 | 0 |
| [118] | D-fructose | 100 | 100 | 100 | 100 | 100 | 100 |
| [119] | L-fucose | 0 | 60 | 50 | 25 | 33 | 75 |
| [120] | D-galactose | 20 | 0 | 50 | 0 | 17 | 25 |
| [121] | Gentiobiose | 40 | 60 | 100 | 25 | 67 | 100 |
| [122] | D-glucose | 100 | 100 | 100 | 100 | 83 | 100 |
| [123] | m-inositol | 0 | 0 | 50 | 0 | 33 | 100 |
| [124] | α-lactose | 0 | 0 | 0 | 0 | 17 | 0 |
| [125] | Lactulose | 0 | 0 | 0 | 0 | 0 | 0 |
| [126] | Maltose | 100 | 100 | 100 | 50 | 100 | 100 |
| [127] | D-mannitol | 0 | 40 | 50 | 0 | 33 | 50 |
| [128] | D-mannose | 100 | 100 | 100 | 25 | 100 | 100 |
| [129] | D-melibiose | 0 | 0 | 0 | 0 | 0 | 0 |
| [130] | β-methylglucoside | 0 | 40 | 75 | 0 | 33 | 0 |
| [131] | Psicose | 80 | 80 | 50 | 50 | 83 | 100 |
| [132] | D-raffinose | 0 | 0 | 0 | 0 | 0 | 0 |
| [133] | L-rhamnose | 0 | 0 | 50 | 0 | 0 | 0 |
| [134] | D-sorbitol | 60 | 60 | 75 | 0 | 83 | 100 |
| [135] | Sucrose | 100 | 80 | 100 | 25 | 83 | 50 |
| [136] | D-trehalose | 100 | 100 | 100 | 0 | 100 | 100 |
| [137] | Turanose | 40 | 80 | 25 | 0 | 100 | 100 |
| [138] | Xylitol | 0 | 20 | 0 | 0 | 0 | 0 |
| [139] | Methyl pyrurate | 60 | 80 | 0 | 100 | 33 | 75 |
| [140] | Monomethylsuccinate | 40 | 20 | 0 | 100 | 0 | 0 |
| [141] | Acetic acid | 100 | 60 | 25 | 75 | 50 | 75 |
| [142] | Cis-aconitic acid | 0 | 0 | 0 | 0 | 0 | 0 |
| [143] | Citric acid | 0 | 0 | 0 | 0 | 0 | 0 |
| [144] | Formic acid | 0 | 0 | 0 | 0 | 0 | 0 |
| [145] | D-galactonic acid lactone | 0 | 0 | 25 | 0 | 0 | 0 |
| [146] | Galacturonic acid | 0 | 0 | 0 | 0 | 0 | 0 |
| [147] | D-gluconic acid | 0 | 0 | 50 | 0 | 0 | 0 |
| [148] | D-glucosaminic acid | 0 | 0 | 50 | 0 | 0 | 0 |
| [149] | D-glucuronic acid | 0 | 0 | 0 | 0 | 0 | 0 |

|  | CHARACTER | CLUSTER | | | | | |
|---|---|---|---|---|---|---|---|
|  |  | 1 | 2 | 3 | 4 | 5 | 6 |
| [150] | α-hydroxybutyric acid | 0 | 0 | 0 | 50 | 0 | 0 |
| [151] | β-hydroxybutyric acid | 0 | 0 | 25 | 100 | 17 | 0 |
| [152] | gamma-hydroxybutyric acid | 0 | 40 | 50 | 75 | 17 | 25 |
| [153] | p-hydroxyphenyl acetic acid | 0 | 0 | 0 | 0 | 0 | 0 |
| [154] | Itaconic acid | 0 | 0 | 0 | 0 | 0 | 0 |
| [155] | α-ketobutyric acid | 100 | 60 | 0 | 100 | 83 | 75 |
| [156] | α-ketoglutaric acid | 0 | 0 | 0 | 25 | 0 | 0 |
| [157] | α-ketovaleric acid | 80 | 20 | 0 | 75 | 0 | 0 |
| [158] | DL-lactic acid | 60 | 20 | 0 | 50 | 17 | 0 |
| [159] | Malonic acid | 0 | 0 | 0 | 25 | 0 | 0 |
| [160] | Propionic acid | 100 | 60 | 50 | 75 | 67 | 75 |
| [161] | Quinic acid | 0 | 0 | 0 | 0 | 0 | 25 |
| [162] | D-saccharic acid | 0 | 0 | 0 | 0 | 0 | 0 |
| [163] | Sebacic acid | 0 | 0 | 0 | 25 | 0 | 0 |
| [164] | Succinic acid | 0 | 0 | 25 | 75 | 17 | 0 |
| [165] | Bromosuccinic acid | 0 | 0 | 0 | 100 | 17 | 0 |
| [166] | Succinamic acid | 40 | 0 | 25 | 75 | 17 | 25 |
| [167] | Glucuronamide | 0 | 0 | 0 | 0 | 0 | 0 |
| [168] | Alaninamide | 80 | 0 | 0 | 0 | 33 | 0 |
| [169] | D-alanine | 0 | 0 | 0 | 0 | 0 | 0 |
| [170] | L-alanine | 0 | 0 | 0 | 0 | 0 | 0 |
| [171] | L-alanylglycine | 0 | 0 | 25 | 0 | 0 | 0 |
| [172] | L-asparagine | 0 | 0 | 25 | 0 | 17 | 25 |
| [173] | L-aspartic acid | 0 | 0 | 25 | 0 | 17 | 0 |
| [174] | L-glutamic acid | 0 | 0 | 0 | 0 | 17 | 0 |
| [175] | Glycyl-L-aspartic acid | 0 | 0 | 0 | 0 | 0 | 0 |
| [176] | Glycyl-L-glutamic acid | 0 | 0 | 0 | 0 | 0 | 0 |
| [177] | L-histidine | 0 | 0 | 0 | 0 | 0 | 0 |
| [178] | Hydroxy L-proline | 0 | 0 | 0 | 0 | 0 | 0 |
| [179] | L-leucine | 20 | 0 | 0 | 0 | 0 | 0 |
| [180] | L-ornithine | 0 | 0 | 0 | 0 | 0 | 0 |
| [181] | L-phenylalanine | 0 | 0 | 0 | 0 | 0 | 0 |
| [182] | L-proline | 0 | 0 | 0 | 0 | 0 | 25 |
| [183] | L-pyroglutamic acid | 0 | 0 | 0 | 0 | 0 | 0 |
| [184] | D-serine | 0 | 0 | 0 | 0 | 0 | 0 |
| [185] | L-serine | 0 | 0 | 0 | 0 | 0 | 0 |
| [186] | L-threonine | 0 | 0 | 0 | 0 | 0 | 0 |
| [187] | DL-carnitine | 0 | 0 | 0 | 0 | 0 | 0 |
| [188] | gamma-aminobutyric acid | 0 | 0 | 25 | 0 | 0 | 0 |
| [189] | Urocanic acid | 0 | 0 | 0 | 0 | 0 | 0 |
| [190] | Inosine | 40 | 20 | 100 | 0 | 33 | 0 |
| [191] | Uridine | 60 | 40 | 100 | 0 | 50 | 0 |
| [192] | Thymidine | 80 | 20 | 50 | 50 | 83 | 0 |
| [193] | Phenylethylamine | 0 | 0 | 0 | 0 | 0 | 0 |

Appendix E

Screening for Proteolytic, Amylolytic and Cellulolytic Enzyme Activity

| STRAIN | PROTEOLYTIC | | | STARCH | CELLULOSE |
|---|---|---|---|---|---|
| | LACTALBUMIN | CASEIN | GELATIN | | |
| Cluster 1 | | | | | |
| 3E.1$^{CT}$ | − | + | + | + | − |
| 71C.4 | n.t. | + | + | + | − |
| 81LN.4 | + | n.t. | + | − | − |
| 60E.4 | + | n.t. | + | + | − |
| wE4 | − | + | + | − | − |
| Cluster 2 | | | | | |
| 69B.4 | n.t. | + | + | + | + |
| RS11$^{CT}$ | n.t. | n.t. | + | + | − |
| RS14 | n.t. | n.t. | + | + | + |
| RS13 | n.t. | n.t. | + | + | + |
| Cluster 3 | | | | | |
| wE1 | − | − | + | + | − |
| wN10 | − | − | + | + | − |
| wN12 | − | − | + | + | − |
| wN16$^{CT}$ | − | − | + | + | − |
| Cluster 4 | | | | | |
| 13C.1 | − | − | − | + | − |
| 23M.1 | − | + | − | − | − |
| 14LN.1 | − | − | − | + | − |
| 15LN.1$^{CT}$ | − | − | − | + | − |
| Cluster 5 | | | | | |
| 66B.4 | + | n.t. | + | + | − |
| AB30 | n.t. | n.t. | n.t. | n.t. | n.t. |
| RS10$^{CT}$ | n.t. | n.t. | + | + | − |
| RS17 | n.t. | n.t. | + | + | − |
| AB49 | n.t. | n.t. | n.t. | n.t. | n.t. |
| AB42 | n.t. | n.t. | n.t. | n.t. | n.t. |
| Cluster 6 | | | | | |
| RS7 | n.t. | n.t. | + | + | − |
| RS8$^{CT}$ | n.t. | n.t. | + | + | − |
| RS15 | n.t. | n.t. | + | + | − |
| RS16 | n.t. | n.t. | + | − | − |

Screening for Proteolytic, Amylolytic and Cellulolytic Enzyme Activity (continued)

| STRAIN | PROTEOLYTIC | | | STARCH | CELLULOSE |
|---|---|---|---|---|---|
| | LACTALBUMIN | CASEIN | GELATIN | | |
| non-clustering | | | | | |
| wE2 | − | − | − | − | − |
| wB3 | − | − | + | − | − |
| 79LN.4 | + | n.t. | + | + | − |
| RS12 | n.t. | n.t. | + | + | − |
| 72C.4 | n.t. | + | + | + | − |
| 80LN.4 | n.t. | + | + | − | − | n.t. = not tested

We claim:

1. A method to prepare an alkali-tolerant enzyme wherein the method comprises
   separating bacteria which have been cultured in a suitable culture medium and recovering enzyme activity from said culture medium,
   wherein said bacteria consist of aerobic, Gram-positive, coccoid, obligate alkaliphilic bacteria having the following characteristics:
   a) forms orange-colored, circular colonies;
   b) grows optimally at about pH 10;
   c) gives a positive response to the following tests:
      1) Gelatin hydrolysis
      2) Penicillin G
      3) Methicillin
      4) Bacitracin;
   d) gives a negative response to the following tests:
      1) N-acetylglucosamine
      2) D-saccharose
      3) Salicin
      4) D-melibiose
      5) Propionate
      6) Glycogen
      7) 3-hydroxybutyrate
      8) Serine
      9) Arginine
      10) Methionine
      11) Valine
      12) Cellobiose.

2. A method to prepare an alkali-tolerant enzyme wherein the method comprises
   separating bacteria which have been cultured in a suitable culture medium and recovering enzyme activity from said culture medium,
   wherein said bacteria consist of aerobic, Gram-positive, short, irregular, rod-shaped, obligate alkaliphilic bacteria having the following characteristics:
   a) forms cream-yellow, small, circular colonies;
   b) grows optimally above pH 8;
   c) gives a positive response to the following tests:
      1) Gelatin hydrolysis
      2) Galactose
      3) β-glucosidase
      4) Arginine
      5) Bacitracin
      6) N-acetyl-D-glucosamine
      7) Cellobiose
      8) Inosine
      9) Uridine;
   d) gives a negative response to the following tests:
      1) Maltose
      2) Acetate
      3) D-glucose
      4) D-melibiose
      5) Propionate
      6) Valerate
      7) Glycogen
      8) Serine
      9) Ampicillin
      10) Penicillin G
      11) Methicillin
      12) Tetracyclin
      13) Methyl pyruvate
      14) Mono-methylsuccinate
      15) α-ketobutyric acid.

3. A method to prepare an alkali-tolerant enzyme wherein the method comprises
   separating bacteria which have been cultured in a suitable culture medium and recovering enzyme activity from said culture medium,
   wherein said bacteria consist of aerobic, Gram-positive, coryneform, obligate alkaliphilic bacteria having the following characteristics:
   a) mature colonies are glistening bright orange/red;
   b) grows optimally between about pH 9 and 10;
   c) gives a positive response to the following tests:
      1) Arginine
      2) Methionine
      3) Glycine
      4) Valine
      5) Methicillin
      6) Tetracyclin
      7) Bacitracin
      8) α-cyclodextrin
      9) Tween 40
      10) Methyl pyruvate
      11) Mono-methylsuccinate
      12) β-hydroxybutyric acid
      13) Bromo-succinic acid;
   d) gives a negative response to the following tests:
      1) Gelatin hydrolysis
      2) Fumarate
      3) Fructose
      4) Galactose
      5) D-saccharose
      6) D-melibiose
      7) Glycogen
      8) L-serine
      9) β-glucosidase
      10) N-acetyl-D-glucosamine
      11) Cellobiose
      12) D-sorbitol
      13) D-trehalose
      14) Turanose.

4. A method to prepare an alkali-tolerant enzyme wherein the method comprises
   separating bacteria which have been cultured in a suitable culture medium and recovering enzyme activity from said culture medium,
   wherein said bacteria consist of aerobic, Gram-positive, coccoid or short rod-shaped, obligate alkaliphilic bacteria consisting essentially of the following characteristics:
   a) cells are often found in pairs, exhibiting a characteristic snapping form of cell division so as to give a V-form arrangement;
   b) no growth below pH 8;
   c) on alkaline-agar, forms opaque, orange colored, punctiform or circular colonies;
   d) in alkaline-broth, growth (37° C.) is flocculent, with the formation of a sediment and surface ring;
   e) grows optimally at above 30° C., no growth above 40° C.;
   f) grows at NaCl concentration of between 0–10%, no growth at a concentration of 12% NaCl;
   g) grows on yeast extract, peptones and carbohydrates;
   h) grows a positive response to the catalase reaction test;
   i) gives a negative response to the following tests:
      1) KOH
      2) Aminopeptidase
      3) Oxidase
      4) Gelatin hydrolysis
      5) Starch hydrolysis.

5. A method to prepare an alkali-tolerant enzyme wherein the method comprises separating bacteria which have been cultured in a suitable culture medium and recovering enzyme activity from said culture medium, wherein said bacteria consist of aerobic, Gram-positive, straight or slightly curved rod-shaped obligate alkaliphilic bacteria consisting essentially of the following characteristics:
  a) cells are sometimes found in pairs, exhibiting a characteristic snapping for of cell division so as to give a V-form arrangement;
  b) no growth below pH 8;
  c) on alkaline-agar forms opaque yellow/ochre-colored circular colonies;
  d) grows between 10° C. and 40° C., no growth at 45° C.;
  e) grows at NaCl concentration of 0–12%, no growth at NaCl concentration of 15%;
  f) grows on yeast extract;
  g) gives a positive response to the following tests:
    1) Catalase reaction
    2) Gelatin hydrolysis;
  h) gives a negative response to the following tests:
    1) KOH
    2) Aminopeptidase
    3) Oxidase
    4) Starch hydrolysis.

6. A method to prepare an alkali-tolerant enzyme wherein the method comprises separating bacteria which have been cultured in a suitable culture medium and recovering enzyme activity from said culture medium, wherein said bacteria consist of aerobic, Gram-positive, straight or slightly curved rod-shaped, obligate alkaliphilic bacteria consisting essentially of the following characteristics:
  a) cells are often found in pairs, sometimes in short chains of 2 to 4 cells;
  b) no growth below pH 7.5;
  c) on alkaline-agar, forms circular, cream-colored colonies;
  d) grows between 10° C. and 45° C., no growth at 50° C.;
  e) grows at NaCl concentration of 0–15%;
  f) gives a positive response to the following tests:
    1) Catalase reaction
    2) Oxidase reaction
    3) Gelatin hydrolysis
    4) Starch hydrolysis;
  d) gives a negative response to the following tests:
    1) KOH
    2) Aminopeptidase.

7. A method to prepare an alkali-tolerant enzyme wherein the method comprises separating bacteria which have been cultured in a suitable culture medium and recovering enzyme activity from said culture medium, wherein said bacteria consist of aerobic, Gram-positive, obligate alkaliphilic bacterium consisting essentially of the following characteristics:
  a) cells are initially spherical, developing into short rods, exhibiting a characteristic snapping form of cell division so as to give a V-form arrangement;
  b) no growth below pH 8;
  c) on alkaline-agar, forms circular, convex, entire, opaque, orange to deep salmon pink colonies;
  d) grows at 10° C. to 37° C., no growth at 40° C.;
  e) grows on yeast extract;
  f) grows at NaCl concentration of 0–12%;
  g) gives a positive response to the following tests:
    1) Catalase reaction
    2) Aminopeptidase
    3) Gelatin hydrolysis;
  h) Gives a negative response to the following tests:
    1) KOH
    2) Oxidase reaction
    3) Starch hydrolysis.

8. A substantially pure enzyme prepared by the method of claim 1.

9. A substantially pure enzyme prepared by the method of claim 2.

10. A substantially pure enzyme prepared by the method of claim 3.

11. A substantially pure enzyme prepared by the method of claim 4.

12. A substantially pure enzyme prepared by the method of claim 5.

13. A substantially pure enzyme prepared by the method of claim 6.

14. A substantially pure enzyme prepared by the method of claim 7.

15. The purified enzyme of claim 8 which has an activity selected from the group consisting of proteolytic, lipolytic and starch-degrading activity.

16. The purified enzyme of claim 9 which has an activity selected from the group consisting of proteolytic, lipolytic and starch-degrading activity.

17. The purified enzyme of claim 10 which has an activity selected from the group consisting of lipolytic and starch-degrading activity.

18. The purified enzyme of claim 11 which has lipolytic activity.

19. The purified enzyme of claim 12 which has proteolytic or starch-degrading activity.

20. The purified enzyme of claim 13 which has an activity selected from the group consisting of proteolytic, lipolytic and starch-degrading activity.

21. The purified enzyme of claim 14 which has an activity selected from the group consisting of proteolytic, lipolytic and starch-degrading activity.

* * * * *